(12) United States Patent
Vieira et al.

(10) Patent No.: US 9,358,204 B2
(45) Date of Patent: Jun. 7, 2016

(54) FORMULATIONS OF VILOXAZINE

(71) Applicant: Supernus Pharmaceuticals, Inc., Rockville, MD (US)

(72) Inventors: Michael L. Vieira, Gaithersburg, MD (US); Austin B. Huang, N. Potomac, MD (US); Padmanabh P. Bhatt, Rockville, MD (US)

(73) Assignee: Supernus Pharmaceuticals, Inc., Rockville, MD (US)

( * ) Notice: Subject to any disclaimer, the term of this patent is extended or adjusted under 35 U.S.C. 154(b) by 0 days.

(21) Appl. No.: 13/761,757

(22) Filed: Feb. 7, 2013

(65) Prior Publication Data

US 2013/0202661 A1 Aug. 8, 2013

Related U.S. Application Data

(60) Provisional application No. 61/596,458, filed on Feb. 8, 2012.

(51) Int. Cl.
*A61K 9/00* (2006.01)
*A61K 9/48* (2006.01)
*A61K 31/5375* (2006.01)

(52) U.S. Cl.
CPC . *A61K 9/00* (2013.01); *A61K 9/485* (2013.01); *A61K 9/4866* (2013.01); *A61K 31/5375* (2013.01)

(58) Field of Classification Search
None
See application file for complete search history.

(56) References Cited

U.S. PATENT DOCUMENTS

| | | | |
|---|---|---|---|
| 3,714,161 A | 1/1973 | Mallion et al. | |
| 4,260,606 A | 4/1981 | Cale, Jr. et al. | |
| 5,558,879 A * | 9/1996 | Chen et al. | 424/480 |
| 5,658,590 A | 8/1997 | Heiligenstein et al. | |
| 6,255,329 B1 | 7/2001 | Maj | |
| 6,667,329 B1 | 12/2003 | Maj | |
| 6,964,962 B2 | 11/2005 | Wong et al. | |
| 2006/0003992 A1 | 1/2006 | Wong et al. | |
| 2006/0246134 A1 | 11/2006 | Venkatesh | |
| 2010/0069390 A1 | 3/2010 | Breder | |
| 2010/0256106 A1 * | 10/2010 | Pasternak et al. | 514/210.02 |
| 2012/0115871 A1 | 5/2012 | Breder | |

FOREIGN PATENT DOCUMENTS

| | | |
|---|---|---|
| GB | 2047096 A | 11/1980 |
| WO | WO 2006/010457 A2 | 2/2006 |
| WO | WO 2007/026219 A2 | 3/2007 |
| WO | WO 2008/061226 A2 | 5/2008 |
| WO | WO 2008/122019 A1 | 10/2008 |
| WO | WO 2008/157094 A1 | 12/2008 |
| WO | WO2010/127120 * | 11/2010 |
| WO | WO 2011/008298 A2 | 1/2011 |

OTHER PUBLICATIONS

Bayliss et al. Br J. Clin Pharmacol pp. 209-214; publication year: 1975.*
Streubel et al. (Expert Opinion Drug Delivery, vol. 3, No. 2, pp. 217-233; publication year: 2006.*
Bayliss et al., "Blood Level Studies with Volixazine Hydrochloride in Man," Br. J. Clin. Pharmac., Jun. 1975, 2(3):209-214.
Chebili et al., "Antidepressants and sexual stimulation: the correlation," Encephale, May-Jun. 1998, 24(3):180-184, English abstract only.
Giles et al., "Characterization of a 5-HT$_{1B}$ receptor on CHO cells: functional responses in the absence of radioligand binding," British Journal of Pharmacology, 1996, 117:1119-1126.
Hedlund et al., "5-HT$_7$ Receptor Inhibition and Inactivation Induce Antidepressantlike Behavior and Sleep Pattern," Biol. Psychiatry, 2005, 58(10):831-837.
Lucchelli et al., "The interaction of antidepressant drugs with enteric 5-HT$_7$ receptors," Naunyn-Schmiedeberg's Arch. Pharmacol., 2000, 362(3):284-289.
Tatsumi et al., "Pharmacological profile of antidepressants and related compounds at human monoamine transporters," European Journal of Pharmacology, 1997, 340(2-3):249-258.
Vanhoenacker et al., "5-HT$_7$ receptors: current knowledge and future prospects," Trends Pharmacol. Sci., 2000, 21(2):70-77.
Altamura et al., "Age, Therapeutic 'Milieu' and Clinical Outcome in Depressive Patients Treated with Viloxazine: A Study with Plasma Levels," Progress in Neuro-Psychopharmacology & Biological Psychiatry, Oxford, GB, 1986, 10:67-75.
Rojo, R. Gomez, "Double blind controlled study of viloxazine and imipramine in depression," Hospital General, 1976, 16(1):27-38, with English summary on p. 37.
Goodman & Gilman's: The Pharmacological Basis of Therapeutics, 10$^{th}$ Edition, 2001, 474-477.

* cited by examiner

*Primary Examiner* — Johann R Richter
*Assistant Examiner* — Katherine Peebles
(74) *Attorney, Agent, or Firm* — Foley & Lardner LLP; Sunit Talapatra

(57) ABSTRACT

Modified release formulations of viloxazine and methods of administering the same are disclosed. High-drug load formulations of viloxazine are further disclosed.

13 Claims, 26 Drawing Sheets

FORMULATIONS OF VILOXAZINE

BACKGROUND OF INVENTION

Viloxazine hydrochloride, (±)-2-[(2-ethoxyphenoxy)methyl]morpholine hydrochloride (Structural Formula 1), is a racemic compound with two stereo isomers (R-viloxazine and S-viloxazine). The molecular weight of the hydrochloride salt is 273.8 with a conversion factor for viloxazine base to viloxazine hydrochloride of 1.154.

Structural Formula 1: Viloxazine Hydrochloride

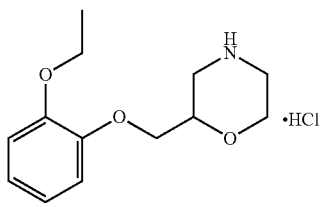 [SMILES: CCOc1ccccc1OCC1CNCCO1 ; Cl]

The pharmacokinetics of viloxazine have been evaluated in six epileptic patients following an intravenous infusion and an oral dose both equivalent to 200 mg of viloxazine base (E. Pisani et al. Psychopharmacology (1986) 90: 295-298). The absolute oral bioavailability was 85% (±14%, standard deviation). The drug was rapidly absorbed following oral administration with a $t_{max}$ of approximately 2 hours. The observed elimination half-life was 4.3 hours (±1.5 hours, standard deviation).

Viloxazine was previously marketed in several European countries for the treatment of major depressive disorder (MDD). Viloxazine is an inhibitor of the reuptake of norepinephrine, but may also enhance the release of serotonin from neuronal stores. The typical "immediate release" oral dose of viloxazine in MDD, expressed as viloxazine base, was 200 mg-300 mg daily given in 2 to 3 divided doses; in certain cases the daily dose was increased to 600 mg (Vidal® pp 2116-2117 (2007)).

Due to the potentially high therapeutic dose, weakly basic nature of the molecule, and a relatively high in vivo clearance rate in humans, viloxazine presents challenges for developing an extended release formulation. These, and other, challenges have been overcome by the formulations of the instant invention.

SUMMARY OF THE INVENTION

Viloxazine hydrochloride, (±)-2-[(2-ethoxyphenoxy)methyl]morpholine hydrochloride, is a racemic compound with two stereo isomers (R-viloxazine and S-viloxazine). In silico physicochemical properties of viloxazine base, calculated using ACD Labs software (product release 8.08), include: a $pK_a$ value of 8.47, a Log P value of 1.10, and an intrinsic solubility value of 2.3 mg/mL for the base. The hydrochloride salt of viloxazine exhibits an aqueous solubility at 37° C. of 78 mg/mL.

In one embodiment, the invention is directed towards modified release formulations of viloxazine. In another embodiment of the invention, the modified release formulation is an extended release formulation. In yet another embodiment, the modified release formulation is a pulsatile release formulation. The pulsatile release may be achieved using a combination of an extended release (XR) component with a delayed release (DR) component, or immediate release (IR) component with an extended release (XR) component, or IR component with a DR component, or IR component with an XR and DR components.

In another embodiment of the invention, modified release formulations of viloxazine with a high drug load are provided. These formulations contain an amount of viloxazine that is from about 25% (w/w) to about 75% (w/w). A further embodiment covers a dosage form comprising the formulation of the current invention in the form of tablets, capsules, beads, granules, powders, caplets, troches, sachets, cachets, pouches, gums, sprinkles, solutions and suspensions. The tablets may be osmotic tablets, matrix tablets, bi- and multi-layer tablets, fast disintegrating tablets, mini-tablets, and other type of tablets commonly used in the art, or a combination thereof. The capsules may contain pellets, beads, tablets, mini-tablets, granules, powders, and/or non-aqueous or partially non-aqueous liquid fill. Capsules may also be soft gelatin capsules comprising non-aqueous or partially non-aqueous liquid fill. The formulation may be also presented in the form of pellets in a capsule, where the capsule can be opened and the pellets sprinkled onto soft food or in a liquid, which is then swallowed.

In yet another embodiment, a formulation is provided comprising viloxazine or a pharmaceutically acceptable salt thereof, and at least one of an extended release component and a delayed release component. The formulation may comprise from 25% (w/w) to 75% (w/w) of viloxazine. Further, the formulation may comprise 10 mg to 800 mg of viloxazine, preferably viloxazine hydrochloride.

The extended release formulation may comprise a release rate controlling compound and at least one pharmaceutically acceptable excipient. The release rate controlling compound may be either a hydrophilic compound or a hydrophobic compound, and preferably incorporated in an amount of from 5% (w/w) to 65% (w/w) of the formulation.

Exemplary hydrophilic compounds include hydroxypropyl cellulose, hydroxypropyl methyl cellulose, methyl cellulose, polyethylene oxide, acacia, acrylic acid derivatives, alginic acid, its salts and derivatives thereof, hydroxyethyl cellulose, povidone, carrageenan, carboxymethylcellulose, tragacanth, polyvinyl alcohol, xanthan gum, and combinations thereof. Exemplary hydrophobic compounds include ethyl cellulose, cellulose acetate, cellulose acetate butyrate, waxes, hydrogenated vegetable oils, glyceryl behenate, glyceryl palmitostearate, PEG glyceryl esters, poly(ethyl acrylate-co-methyl methacrylate) ethyl acrylate methyl methacrylate copolymer, poly(ethyl acrylate-co-methyl methacrylate-cotrimethylammonioethyl methacrylate chloride), polyvinyl acetate, cellulose acetate propionate, and combinations thereof.

The formulation may comprise a matrix core, wherein the matrix core comprises an admixture of viloxazine and the release rate controlling compound. The core comprising viloxazine may have a coating of the hydrophobic compound on top of the core. Alternatively, the core comprising viloxazine may have a coating of an enteric compound on top of the core.

The formulation may further comprise a delayed-release coating comprising an enteric compound and/or at least one additional viloxazine-containing component selected from an immediate release component, an extended release component and a delayed release component comprising an enteric compound. The delayed release component may comprise at least one core comprising viloxazine and a coating of the enteric compound on top of the core(s).

Each component of the formulation may be in the form of a layer and/or a plurality of particles. The formulation may thus comprise an extended release component, an immediate release component and a delayed release component. As well, the formulation may comprise at least two extended release components, wherein each extended release component has its own rate of release.

Enteric compounds may be selected from a group consisting of poly(methyl acrylate-co-methyl methacrylate-co-methacrylic acid), poly(methacrylic acid-co-methyl methacrylate), hydroxypropyl methylcellulose acetate succinate, hydroxypropyl methylcellulose phthalate, cellulose acetate phthalate, shellac, and zein and comprise from 5% (w/w) to 40% (w/w) of the formulation.

Further, the present invention provides extended release dosage formulations of viloxazine base, and/or its salts, stereoisomers and polymorphs thereof for administration to a mammal in need thereof for the treatment of CNS disorders, including but not limited to the treatment of ADHD and major depressive disorders. The formulations may be administered once a day (QD) or twice a day (BID) and can result in a reduced level of at least one undesirable side effect as compared to the same amount of viloxazine administered as an immediate release formulation BID or TID. The undesirable side effects may be, for example, gastrointestinal side effects (e.g., dyspepsia, nausea and vomiting) and neurological side effects (e.g., sleep disturbances, insomnia, abnormal dreams). The mammal being treated may be a human child or adult administered the viloxazine formulation in a dose of from 10 mg to 800 mg of viloxazine.

The administration of the present formulations provides for a maximum steady state plasma concentration (Cmax) of viloxazine which is higher than the minimal therapeutically effective concentration and is in the range of 50% to 125% relative to the maximum plasma concentration produced by administration of viloxazine as an IR formulation BID or TID. The formulations also provide for relative steady state area under the viloxazine plasma concentration time profiles for a 24 hour dosing interval (AUCtau) in the range of 80% to 125% as compared to viloxazine administered as an immediate release formulation TID or BID.

In an additional embodiment, the invention also provides a dosage form of viloxazine that can provide therapeutic levels of the drug for the period of time from about 4 hours to about 24 hours, preferably from about 6 hours to 16 hours, and most preferably from about 8 hours to 16 hours.

Further, the present invention provides extended release dosage forms that overcome the surprising lower mean relative bioavailability observed in a clinical study. As well, formulations of the instant invention may be characterized by a lower incidence of the adverse effects including but not limited to gastrointestinal and neurological side effects.

DEFINITIONS

Figure 1:
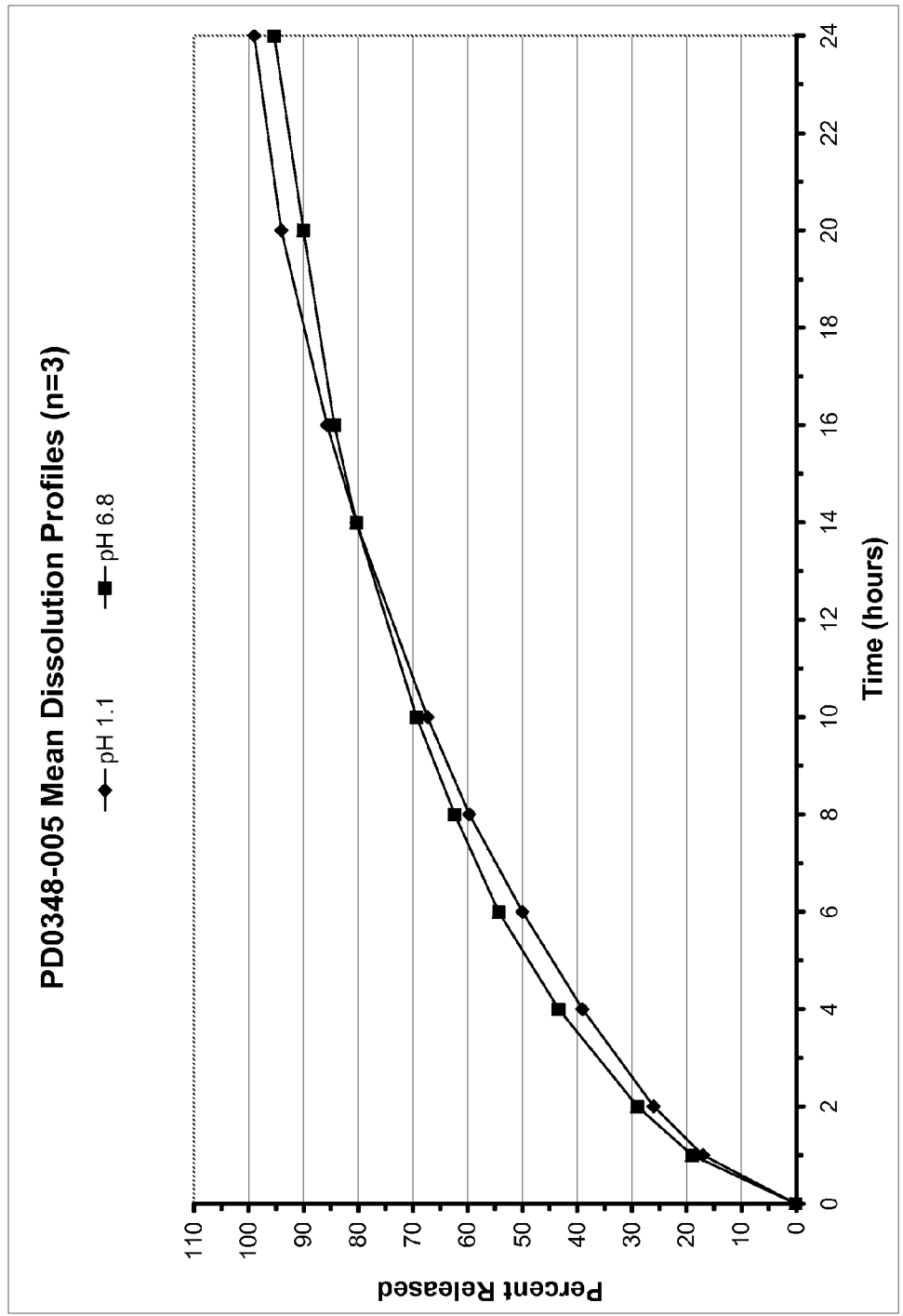
FIG. 1 shows the mean dissolution profiles (n=3) of a 200 mg dose strength tablet (PD0348-005) at pH 1.1 and pH 6.8 (Example 1).

Unless otherwise specified, "a" or "an" means "one or more" in the present application.

The term "Viloxazine," unless specified otherwise, means (RS)-2-[(2-ethoxyphenoxy)methyl]morpholine or a pharmaceutically acceptable salt or ester thereof, any polymorph thereof as well as variable mixtures of the R and S enantiomers or either one of the R or S enantiomers in a substantially pure form.

An "immediate release formulation" refers to a formulation that releases greater than or equal to 80% by weight of the active pharmaceutical agent in less than or equal to 1 hour.

The term "modified release" encompasses any mode of release that is different from an immediate release.

In the current application, the term "enteric compound" is used to mean a compound having solubility that is pH-dependent.

The term "particles", as used herein, includes, without any limitations on the nature and size thereof, any particles, spheres, beads, granules, pellets, mini-tablets, particulates.

The term "extended release" refers to at least 80% of the drug substance being released from the formulation over a period of time of at least 2 hours either in vitro, as in a dissolution test, or in vivo following oral ingestion of the drug containing entity.

The term "delayed release" refers to a formulation where there is substantially no release of the drug substance at a pH below 4.5, but the drug substance is released when the formulation is exposed to a pH of 4.5 or above.

The term "core" refers to the internal foundation of a structural unit (e.g., a bead) with or without drug.

The term "pharmaceutically acceptable excipient" refers to those substances that are well accepted by the industry and regulatory agencies such as those listed in monographs published in compendia such as *USP—NF, Food Chemicals Codex, Code of Federal Regulations (CFR), FDA Inactive Ingredients Guide* and in 21 CFR parts 182 and 184 that lists substances that are generally regarded as safe (GRAS) food ingredients.

The term "high drug load" for a drug substance in the current application applies to the formulations where the drug substance in the composition represents at least 25% (w/w).

"Soluble drug substance" is defined as per the USP definition for soluble substances—1 part of substance is soluble in 10 to 30 parts of solvent.

For the purpose of this application, the terms "sieve size" or "mesh size" are used interchangeably and follow the designations of the US Standard sieves.

DETAILED DESCRIPTION OF THE INVENTION

The formulations of the instant invention provide modified release compositions of viloxazine comprising viloxazine, at least one release rate controlling compound or an enteric compound, or a combination thereof, and at least one pharmaceutically acceptable excipient. Further, the invention provides modified release formulations of viloxazine with a high drug load.

The modified release formulations of viloxazine exhibit an XR profile, or a DR profile, or a combination of an XR and a DR profile, or any combination of these with an IR profile. In some embodiments, the formulations may exhibit a pulsatile release profile. These specific release profiles are achieved by formulating viloxazine with at least one of a release rate controlling compound and/or an enteric compound, and at least one excipient in a variety of inventive formulations.

The release rate controlling compounds of the current invention may be selected from hydrophilic rate controlling compounds and hydrophobic rate controlling compounds. The following non-limiting examples of such compounds are provided below.

Hydrophilic compounds: hydroxypropyl cellulose, hypromellose (hydroxypropyl methyl cellulose), methyl cellulose, polyethylene oxide, acacia, acrylic acid derivatives, alginic acid (and its salts and derivatives thereof), hydroxyethyl cellulose, povidone, carrageenan, carboxymethylcellulose, tragacanth, polyvinyl alcohol, xanthan gum and combinations thereof.

Hydrophobic compounds: ethyl cellulose, cellulose acetate, cellulose acetate butyrate, waxes (e.g., carnauba wax, microcrystalline wax), hydrogenated vegetable oils, Compritol 888 ATO (glyceryl behenate), Precirol ATO 5 (glyceryl palmitostearate), PEG glyceryl esters such as Gelucire 50/1, EUDRAGIT® NE 30 D or EUDRAGIT® NM 30 D (poly (ethyl acrylate-co-methyl methacrylate) ethyl acrylate methyl methacrylate copolymer), EUDRAGIT® RS and EUDRAGIT® RL (poly(ethyl acrylate-co-methyl methacrylate-cotrimethylammonioethyl methacrylate chloride)), polyvinyl acetate, cellulose acetate propionate, and combinations thereof.

The enteric compounds of the current invention may be selected from the following non-limiting list of such compounds:

Enteric compounds: EUDRAGIT® FS 30 D (poly(methyl acrylate-co-methyl methacrylate-co-methacrylic acid)), EUDRAGIT® L 30 D-55, EUDRAGIT® L and EUDRAGIT® S (poly(methacrylic acid-co-methyl methacrylate)), hydroxypropyl methylcellulose acetate succinate, hydroxypropyl methylcellulose phthalate, cellulose acetate phthalate, shellac, zein, and combinations thereof.

The release rate controlling compounds, enteric compounds or combinations thereof may be included into the formulation in the amount of from 5% to 65%, preferably in the amount of from 5% to 55%, most preferably in the amount of from 5% to 50%, by weight of the formulation.

Compounds that can be used as release rate controlling coatings include: cellulose esters, cellulose acetate, cellulose acetate butyrate, ethyl cellulose, EUDRAGIT® RS and EUDRAGIT® RL (poly(ethyl acrylate-co-methyl methacrylate-cotrimethylammonioethyl methacrylate chloride)), EUDRAGIT® NE 30 D or EUDRAGIT® NM 30 D (poly (ethyl acrylate-co-methyl methacrylate)), ethyl acrylate methyl methacrylate copolymer, polyvinyl acetate and combinations thereof.

In addition, the following enteric compounds can be used in a coating to provide a delay in the release profile: EUDRAGIT® FS 30 D (poly(methyl acrylate-co-methyl methacrylate-co-methacrylic acid)), EUDRAGIT® L 30 D-55 (methacrylic acid-ethyl acrylate copolymer dispersion), EUDRAGIT® L and EUDRAGIT® S (poly(methacrylic acid-co-methyl methacrylate)), hydroxypropyl methylcellulose acetate succinate, hydroxypropyl methylcellulose phthalate, cellulose acetate phthalate, shellac, zein, and combinations thereof.

The application of a release rate controlling compound coating or an enteric compound coating is achieved using standard coating techniques such as spraying, dipping, casting, coating solvent evaporation, molding or compression coating.

The release rate controlling and enteric compounds described above may be used to prepare a variety of modified release systems:

A) Matrix Systems, wherein an active pharmaceutical ingredient (viloxazine, or viloxazine and an additional active); at least one release rate controlling compound and at least one pharmaceutically acceptable excipient are homogeneously intermixed to form a matrix. Hydrophilic and hydrophobic compounds listed above may be used to prepare these viloxazine-containing matrices. These matrices may be presented in the form of matrix tablets, matrix multiparticulates, or in the form of a layer coated onto a substrate.

Matrix tablets may be in the form of multiple layer tablets (e.g., bilayer or tri-layer tablets), tablet within a tablet, encapsulated mini-tablets or a tablet of compressed modified release particles. These matrix systems may be coated with release rate controlling compounds and/or the enteric compounds to add additional release rate controlling characteristics or a delayed release characteristics to the extended release profile of a formulation.

B) Drug-Layered Systems that comprise an inert core and at least one drug-containing layer coated onto this core. The drug containing layer(s) may be further coated with a layer of a release rate controlling compound selected from those listed above. If the drug-containing layer of the drug-layered system does not contain any release rate controlling compounds and is of an immediate release nature, then a release rate controlling coating is necessary for achieving the modified profiles of the current invention.

In cases where the drug-containing layer is an extended release matrix layer described above, the release rate controlling coating is optional and allows for additional modification of the release profile. For example, the coating may be used to modulate the release (slow initially, faster later; or fast initially, slower later), or to provide a delay in the release. In particular the release rate controlling coatings can include: cellulose esters, cellulose acetate, cellulose acetate butyrate, ethyl cellulose, EUDRAGIT® RS and EUDRAGIT® RL (poly(ethyl acrylate-co-methyl methacrylate-cotrimethylammonioethyl methacrylate chloride)), EUDRAGIT® NE 30 D or EUDRAGIT® NM 30 D (poly(ethyl acrylate-co-methyl methacrylate)), ethyl acrylate methyl methacrylate copolymer, polyvinyl acetate, cellulose acetate propionate, and combinations thereof.

In addition, the following enteric compounds can be used in a coating to provide a delay in the release profile: EUDRAGIT® FS 30 D (poly(methyl acrylate-co-methyl methacrylate-co-methacrylic acid)), EUDRAGIT® L 30 D-55 (methacrylic acid-ethyl acrylate copolymer dispersion), EUDRAGIT® L and EUDRAGIT® S (poly(methacrylic acid-co-methyl methacrylate)), hydroxypropyl methylcellulose acetate succinate, hydroxypropyl methylcellulose phthalate, cellulose acetate phthalate, shellac zein, and combinations thereof.

In some embodiments of the invention, a core may not be inert but compositionally be of pure drug substance or a mixture of the drug substance and one or more pharmaceutically acceptable excipient producing an IR core. In such a case, the cores can undergo further processing as described above for inert cores to produce the desired extended release formulation.

Processes that may be used to produce formulations of this embodiment comprising a drug-containing core include solution or dry powder drug layering, compression coating, hot melt coating, supercritical fluid coating, electrostatic spray coating, agglomeration, granulation, pelletization, roller compaction, tablet compression, wet granulation with extrusion and spheronization, hot melt extrusion, and injection molding. Roller compaction, tablet compression, and the extrusion with spheronization processes are particularly helpful for the manufacturing of formulations with a high drug load.

Without putting any limitations thereon, exemplary formulations of the present invention having different modified pharmacokinetic (PK) profiles for viloxazine are as follows:

Mixed IR and XR particles in a capsule, compressed tablet or any other dosage form (IR/XR mixed particles). The IR particles provide the initial release of the therapeutic agent followed by extended release from the XR particles (IR/XR mixed population of particles).

A single population of particles in a capsule, compressed tablet or any other dosage form where the particles are either matrix XR particles, or IR cores further comprising an XR coating.

Mixed particles in a capsule, compressed tablet or any other dosage form where XR particles of differing drug release characteristics are combined.

Mixed particles in a capsule, compressed tablet or any other dosage form where DR particles of differing drug release characteristics are combined, optionally resulting in a pulsatile profile.

Mixed particles in a capsule, compressed tablet or any other dosage form where IR particles are mixed with DR particles (IR/DR mixed particles). The IR particles provide the initial release of the therapeutic agent followed by release from the DR particles resulting in pulsed PK profiles. (IR/DR mixed population of particles)

A single population of particles in a capsule, compressed tablet or any other dosage form where the pellet incorporates an IR core coated with DR coat, which is further coated with an IR drug layer. The outer IR drug layer provides an immediate release of the therapeutic agent followed by a delayed release from the DR core resulting in pulsed PK profile. (IR/DR single population of particles)

Mixed particles in a capsule, compressed tablet or any other dosage form where IR particles are mixed with DR coated XR particles (IR/DR-XR). The IR particles provide the initial release of the therapeutic agent followed by delayed and extended release from the DR coated XR particles. (IR/DR-XR mixed population of particles)

A single population of particles in a capsule, compressed tablet or any other dosage form where the pellet incorporates an IR core coated with XR coat, which is coated with DR coat that is subsequently drug layered. The outer drug layer provides the initial immediate release of the therapeutic agent followed by delayed and extended release from the remainder of the pellet. (IR/DR-XR single population of particles)

Mixed particles in a capsule, compressed tablet or any other dosage form where XR particles are mixed with DR particles. The XR provides the initial and continuing release of the therapeutic agent followed by release from the DR particles. (XR/DR mixed population of particles)

A single population of particles in a capsule, compressed tablet or any other dosage form where the pellet incorporates IR core coated with a DR coat which is then coated with a drug layer that is subsequently coated with an XR coat to produce a fast XR layer. The fast XR outer layer provides the initial release of the therapeutic agent followed by delayed release from the DR core. (XR-f/DR single population of particles).

An XR tablet, which is either a matrix tablet or an XR-coated tablet.

A DR tablet coated with an IR drug layer.

One or more than one DR tablets mixed with one or more IR tablets in a capsule.

XR tablet coated with a DR coat, then coated with an IR drug layer.

A bi-layer tablet with one layer containing the drug in XR form and a $2^{nd}$ layer containing the drug in an IR form.

A bi-layer tablet with one layer containing the drug in XR form and a $2^{nd}$ layer containing the drug in DR form.

A DR coated matrix tablet providing a DR/XR profile.

(C) Osmotic Release Systems.

In a further embodiment, the invention provides an extended release viloxazine preparation in the form of an osmotic tablet, wherein the drug release rate is determined by the rate of water permeation into the tablet core through a semi-permeable membrane coating.

For the preparation of an osmotic tablet, viloxazine may be mixed with osmotic agent(s), tableting aides such as diluents and lubricants, and other commonly used excipients. The mixture is tableted either by direct compression or granulation followed by compression. Tablets are then coated with at least one release rate controlling compound that forms a semi-permeable membrane that surrounds each tablet.

The semipermeable membrane, which surrounds the drug-containing core, comprises at least one release rate controlling compound selected from following cellulose esters, cellulose ethers and cellulose ester ethers. Non-limiting examples of such compounds include cellulose acylate, cellulose ethyl ether, cellulose diacylate, cellulose triacylate, cellulose acetate, cellulose diacetate, cellulose triacetate, mono-, di- and tricellulose alkyls, mono-, di- and tricellulose aroyls, and the combinations thereof. Additional release rate controlling compounds include ethyl cellulose, EUDRAGIT® RS and EUDRAGIT® RL (poly(ethyl acrylate-co-methyl methacrylate-cotrimethylammonioethyl methacrylate chloride), and EUDRAGIT® NE 30 D or EUDRAGIT® NM 30 D poly(ethyl acrylate-co-methyl methacrylate), ethyl acrylate methyl methacrylate copolymer.

The semi-permeable membrane may be applied on the tablets using standard coating techniques such as spraying, dipping, casting, coating solvent evaporation, molding or compression coating. An orifice is then drilled in the tablet coat using laser tablet drilling system or other mechanical means to allow the release of drug from the core.

Osmotic agents used for the practice of the current invention are well known in the art and include non-swellable compounds represented by, but not limited to polyols, carbohydrates (including monosaccharides, oligosaccharides, polysaccharides and sugar alcohols), acids, salts and hydrophilic compounds. For example, osmotic agents may be selected from mannitol, maltrin, xylitol, maltitol, lactitol, isomalt, sorbitol, arabitol, erythritol, ribitol, insositol, trehalose, lactose, glucose, sucrose, raffinose, fructose, dextran, glycine, urea, citric acid, tartaric acid, ascorbic acid, aspartame, malic acid, sodium chloride, potassium chloride, magnesium chloride, disodium hydrogen phosphate, sodium phosphate, potassium phosphate, sodium sulfate, lithium sulfate, magnesium sulfate, magnesium succinate, sodium bicarbonate, sodium carbonate, sodium acetate, sodium ascorbate, polyethylene glycol, maltodextrin, cyclodextrins and derivatives, non-swelling block polymers of PEO and PPO, polyethylene glycols, cellulose ethers, and combinations thereof.

Osmotic tablets can be formulated as a single or as a multiple layer core. In one embodiment, the osmotic tablet comprises a bilayer core, wherein one layer comprises agents to modulate drug release, such as a solubilizer, that are released in an extended manner, and the second layer comprises the drug and potentially other agents to modulate drug release.

An overcoat of drug can be applied to the tablet following functional coating to provide an immediate release component to the dosage form. Alternatively, the osmotic tablet may be coated with an enteric compound on top of the semipermeable membrane providing a DR/XR profile.

In addition to the release rate controlling compounds, a number of pharmaceutically acceptable excipients may be used in the formulations of the invention as disclosed above. These excipients are well known in the art, and include binders and diluents, such as povidone, starch, gelatin, maltodextrin, methylcellulose, hydroxypropyl cellulose, hydroxypropyl methylcellulose, carboxymethylcellulose, sucrose, dextrose, acacia, tragacanth and locust bean gum, microcrystalline cellulose, dicalcium phosphate, calcium sulfate, cellulose, and talc; lubricants such as sodium stearyl fumarate and the metallic stearates such as magnesium stearate; wetting and solubilizing agents such as sodium docusate, sodium lauryl sulfate, polyethylene glycol, lecithin, poloxamer, polysorbates, polyoxyethylene ethers and sorbitan esters; disintegrants such as crosslinked sodium carboxymethylcellulose, sodium starch glycolate and crospovidone; buffering agents and/or pH modulating agents, such as aluminum hydroxide, ammonium bicarbonate, ammonium carbonate, ammonium phosphate, arginine, calcium acetate, calcium ascorbate, magnesium acetate, magnesium carbonate, potassium acetate, potassium bicarbonate, potassium carbonate, potassium phosphate dibasic, potassium sodium tartrate, potassium citrate, sodium citrate, sodium phosphate monobasic, sodium phosphate dibasic, sodium phosphate tribasic, sodium acetate, sodium bicarbonate, sodium ascorbate, sodium carbonate, fumaric acid, malic acid, tartaric acid, ascorbic acid, aspartic acid, alginic acid, glutamic acid, sorbic acid, and succinic acid; and glidants such as talc, starch and colloidal silicon dioxide; pore formers modulating the permeability of the semipermeable rate controlling membrane such as povidone, hypromellose, hydroxyethyl cellulose, hydroxypropyl cellulose, organic acids and salts amongst other excipients.

(D) Gastro-Retentive Systems.

In a further embodiment, the invention provides an extended release viloxazine preparation in the form of a gastro-retentive tablet, in particular a gastro-retentive extended release tablet. The gastro-retentive tablet is designed to be retained in the stomach for up to 6 hours after ingestion, after which the remaining dosage form and essentially all undissolved drug is released into the duodenum to transit through the gastrointestinal tract. The in-vitro dissolution profile used for the GR-ER tablet releases 80% of the dose of drug contained in the dosage form in approximately 10 hours.

Formulations of the instant invention are characterized by a lower incidence of gastrointestinal side effects such as dyspepsia, nausea and vomiting and neurological side effects including sleep disturbances such as insomnia and abnormal dreams.

It was further unexpectedly discovered during the development of the inventive formulations that the water solubility and dissolution rate of a viloxazine salt may be influenced by the addition of a common ion into the formulation. For example, the dissolution rate and solubility of viloxazine hydrochloride is influenced by the addition of chloride containing substances such as sodium chloride, potassium chloride, calcium chloride or magnesium chloride, or other chloride salts (Example 12).

Another aspect of the present invention is the treatment of CNS disorders in mammalian subjects, including but not limited to the treatment of ADHD, ADHD related disorders and depressive disorders, with modified release formulations of viloxazine as described herein. One treatment regimen comprises administering the viloxazine formulation of the current invention to a subject once or twice a day to provide a total daily dose ranging from 10 mg to 800 mg of viloxazine (base).

In an additional embodiment, the invention also discloses formulations of viloxazine that can provide therapeutic levels of the drug for the period of time from 4 to 24 hours, or for the periods of from 8 to 20 hours, or for the periods of from 12 to 16 hours.

Formulations of the instant invention are characterized by a maximum steady state plasma concentration ($C_{max}$) of viloxazine which is higher than the minimal therapeutically effective concentration and is in the range of 50% to 125% relative to the maximum plasma concentration produced by the administration of from 100 mg to 600 mg, in particular, of from 150 mg to 300 mg, of from 300 mg to 450 mg, of from 450 mg to 600 mg of viloxazine as an IR formulation three times daily (TID) or twice daily (BID). In one embodiment, the novel formulations provide for a relative $C_{max}$ in the range of 80% to 125%, as compared to viloxazine administered as an IR formulation TID or BID. In the other embodiment, the invention provides for the $C_{max}$ which is lower than the maximum plasma concentration produced by viloxazine administered as an IR formulation TID or BID.

Further, the formulations of the instant invention are characterized by a maximum steady state plasma concentration ($C_{max}$) of viloxazine in the range of from 1.5 µg/mL to 11 µg/mL, in particular in the range of from 1.5 µg/mL to 3 µg/mL, or of from 3 µg/mL to 6 µg/mL; or of from 6 µg/mL to 9 µg/mL, or from 9 µg/mL to 11 µg/mL.

The formulations of the current invention also provide relative steady state area under the viloxazine plasma concentration—time profiles for a 24 hour dosing interval ($AUC_{tau}$) in the range of 80% to 125% as compared to viloxazine administered as an IR formulation TID or BID. Further, the formulations of the instant invention are characterized by $AUC_{tau}$ in the range of 80% to 125%, of the AUC achieved by the selected IR dosing scheme.

Additionally, the present invention provides extended release dosage forms that overcome the surprising lower mean relative bioavailability observed in a clinical pilot PK study in healthy human subjects of the extended release formulations of Example 15 as compared to the immediate release formulation dosed in the study. This effect was accomplished by constructing the extended release dosage forms by the careful selection of viloxazine dose to be delivered and the in vitro dissolution profile of the extended release dosage form such that the relative viloxazine systemic in vivo exposure achieved at steady state for the extended release dosage form, as measured by the viloxazine plasma concentration—time profile for a 24 hour dosing interval ($AUC_{tau}$), is 80% to 125% of that achieved by viloxazine dosed as immediate release formulation three times daily (TID) or twice daily (BID).

In a further embodiment, the invention discloses a method of treatment of the CNS disorders such as listed above with high-drug load formulations of viloxazine exhibiting modified release. These formulations are characterized by the amount of viloxazine in the finished drug product from about 25% w/w to about 75% w/w, or from about 30% (w/w) to about 60% (w/w), or from about 40% (w/w) to about 50% (w/w).

The method results in the reduced frequency of administration and in the diminishing number of units that should be taken by the patient, and thus in better compliance and treatment outcomes.

The invention is further illustrated by, though in no way limited to, the following examples.

EXAMPLES

Example 1

Extended Release Matrix Tablet of Viloxazine (PD0348-005)

The manufacturing process for the matrix tablet included preparation of a wet granulation (Glatt table top granulator—1 L bowl) of viloxazine hydrochloride, hypromellose (METHOCEL™ K15M) and microcrystalline cellulose (Avicel® PH101) using a solution of a low molecular weight hypromellose (METHOCEL™ E5) and water as the granulating medium. The wet granulation was oven dried at 40° C. to a moisture level of less than 1% (w/w) and then sized by passing through an 18 mesh sieve. The sieved material was then blended with additional microcrystalline cellulose (Avicel® PH 102), colloidal silicon dioxide, NF, talc, USP and magnesium stearate, NF producing the final tablet blend formulation PD0348-005 (Table 1). The final tablet blend was compressed into extended-release tablets at the dose strengths of 50 mg and 200 mg (as viloxazine base).

TABLE 1

Formulation PD0348-005

| Compressed Tablet [a] | Usage (% w/w) |
|---|---|
| Viloxazine Hydrochloride | 34.60 |
| METHOCEL ™ K15M Premium CR | 31.59 |
| Avicel ® PH 101 | 14.24 |
| Avicel ® PH 102 | 12.53 |
| METHOCEL ™ E5 Premium LV | 2.04 |
| Talc, USP | 3.00 |
| Colloidal Silicon Dioxide, NF | 1.00 |
| Magnesium Stearate, NF | 1.00 |
| Total | 100 |

[a] Drug load 35% (w/w) viloxazine hydrochloride

The 200 mg dose strength tablet formulation was evaluated for dissolution (FIG. 1). These compressed tablets exhibited consistent content uniformity. The dissolution profile of PD0348-005 was pH independent, exhibiting extended-release with a $t_{80}$ (time to release 80% label claim) of 14 hours.

Example 2

Effect of the Higher Drug Loads on the Drug Release

Tablet PD0348-005 was reformulated to study the effect of higher drug loads on the drug release from the matrix. The content of viloxazine hydrochloride was increased to 40% (w/w) in formulation PD0348-069 and 45% (w/w) in formulation PD0348-071 while reducing the amount of Avicel® but maintaining the same amount of METHOCEL™ K15M. These tablets were manufactured in a similar manner as PD0348-005.

TABLE 2

Formulation PD0348-069 (200 mg dose strength)

| Compressed Tablet [a] | Usage (% w/w) |
|---|---|
| Viloxazine Hydrochloride | 40.00 |
| METHOCEL ™ K15M Premium CR | 30.00 |
| Avicel ® PH 101 | 23.00 |
| METHOCEL ™ E5 Premium LV | 3.00 |
| Talc, USP | 3.00 |
| Magnesium Stearate, NF | 1.00 |
| Total | 100 |

[a] Drug load 40% (w/w) viloxazine hydrochloride

TABLE 3

Formulation PD0348-071 (200 mg dose strength)

| Compressed Tablet [a] | Usage (% w/w) |
|---|---|
| Viloxazine Hydrochloride | 44.99 |
| METHOCEL ™ K15M Premium CR | 30.00 |
| Avicel ® PH 101 | 18.00 |
| METHOCEL ™ E5 Premium LV | 3.00 |
| Talc, USP | 3.00 |
| Magnesium Stearate, NF | 1.00 |
| Total | 100 |

[a] Drug load 45% (w/w) viloxazine hydrochloride

Figure 2:
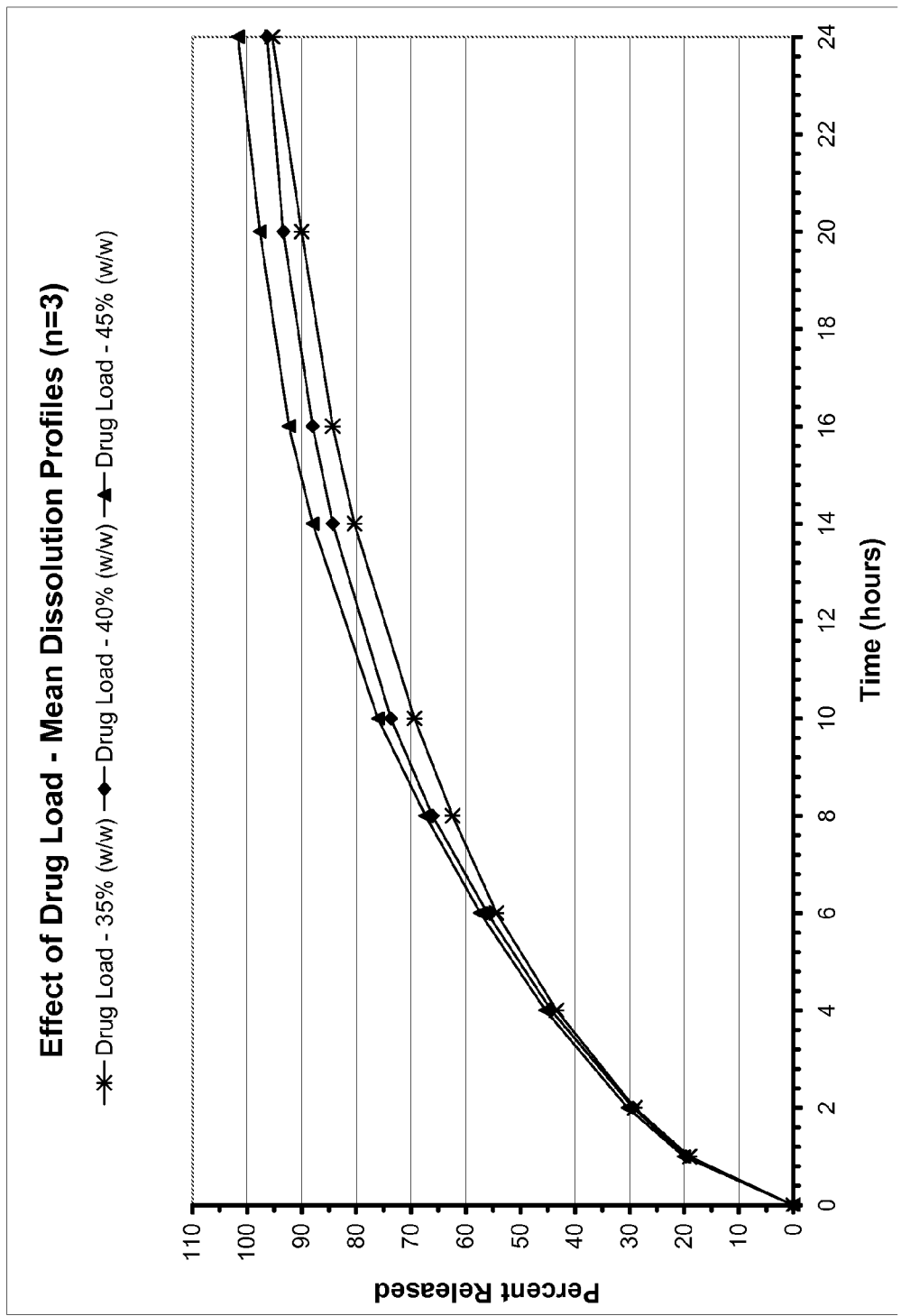
FIG. 2 shows the effect of drug load on the mean dissolution profiles (n=3) of 200 mg dose strength tablets (PD0348-005 (35% w/w), PD0348-069 (40% w/w) and PD0348-071 (45% w/w)) at pH 6.8 (Example 2).

Formulations PD0348-069 and PD0348-071 were subjected to dissolution testing (n=3) at pH 6.8 and the profiles (FIG. 2) were compared to PD0348-005 using the similarity factor test ($f_2$) using the following equation (Guidance for Industry SUPAC-MR: Modifies Release Solid Oral Dosage Forms, CDER September 1997):

$$f_2 = 50 \log \{[1 + 1/n \Sigma_{t=1}^{n}(R_t - T_t)^2]^{-0.5} \times 100\}$$

Wherein: n is the number of time points (n=8)

R is the reference formulation (PD0348-005); and

T is the test formulation (PD0348-069 or PD0348-071)

The $f_2$ values calculated for PD0348-069 and PD0348-071 were 74 and 67, respectively. An $f_2$ value between 50 and 100 suggests that the dissolution profile of the test formulation is similar to that of the reference formulation.

Additional matrix tablet dose strengths are possible, for example PD0348-071 can be compressed into reasonable sized tablets for dose strengths of 100 mg, 300 mg, 400 mg or 600 mg.

Example 3

Dissolution Testing of the Matrix Tablet

TABLE 4

Formulation PD0348-015

| Compressed Tablet [a] | Usage (% w/w) |
|---|---|
| Viloxazine Hydrochloride | 34.60 |
| POLYOX ™ WSR 303 | 30.00 |
| Avicel ® PH 101 | 21.62 |
| Avicel ® PH 102 | 5.03 |
| METHOCEL ™ E5 Premium LV | 3.75 |
| Talc, USP | 3.00 |
| Colloidal Silicon Dioxide, NF | 1.00 |
| Magnesium Stearate, NF | 1.00 |
| Total | 100 |

[a] Drug load 35% (w/w) viloxazine hydrochloride

Figure 3:
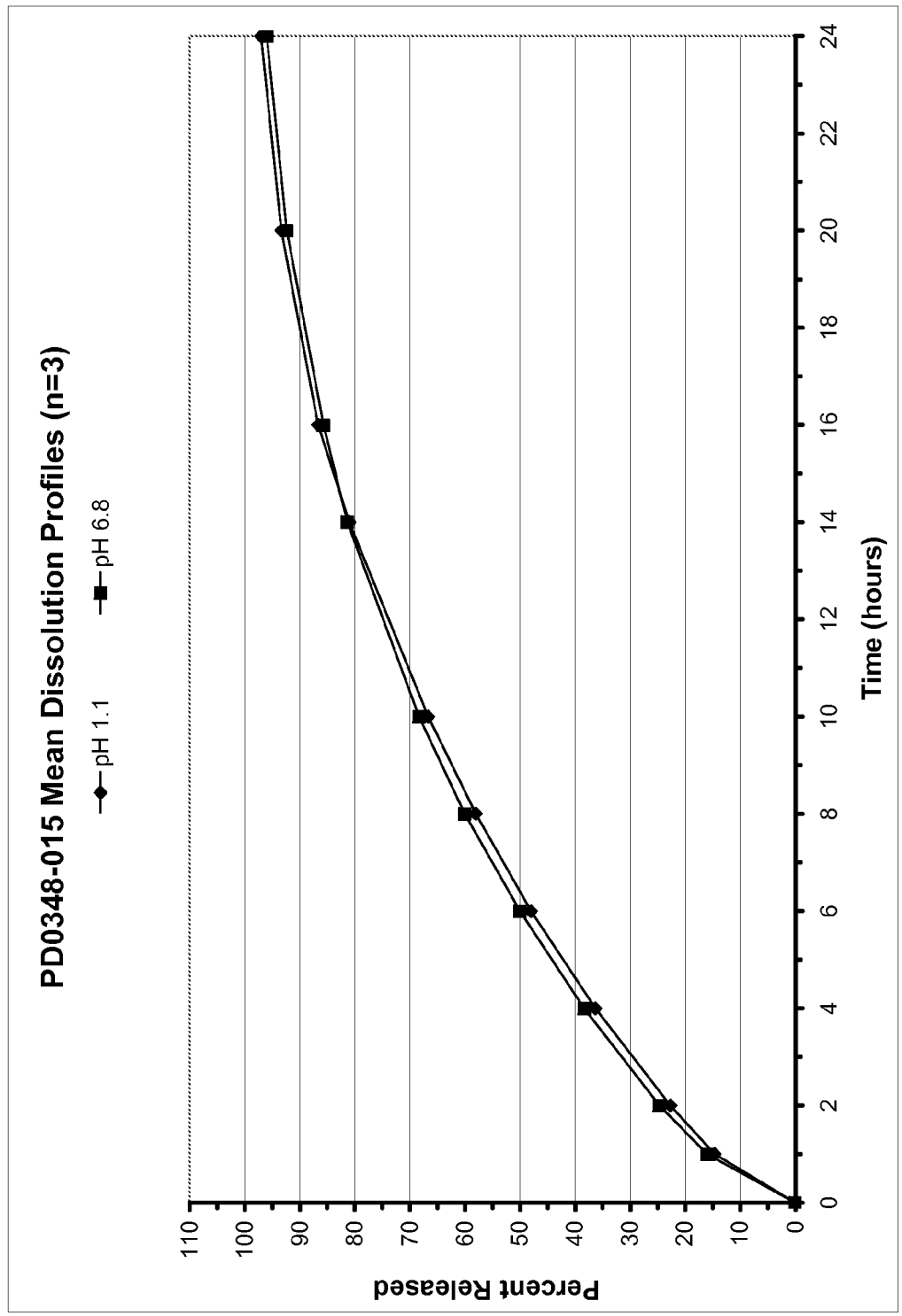
FIG. 3 shows the mean dissolution profiles (n=3) of a 200 mg dose strength tablet (PD0348-015) at pH 1.1 and pH 6.8 (Example 3).

The manufacture of the final tablet blend for PD0348-015 was similar to that of PD0348-005. PD0348-015 was compressed into 50 mg and 200 mg dose strength tablets. The 200 mg dose strength tablet was evaluated for drug release by dissolution testing (n=3) at both pH 1.1 and pH 6.8 (FIG. 3). The dissolution profile of PD0348-015 was pH independent exhibiting extended-release with a $t_{80}$ of 14 hours.

Example 4

Extended Release Matrix Tablet of Viloxazine (PD0348-041)

TABLE 5

Formulation PD0348-041 (200 mg dose strength)

| Compressed Tablet | Usage (% w/w) |
|---|---|
| Viloxazine Hydrochloride | 34.60 |
| EUDRAGIT ® NE 30 D (solids) | 12.04 |
| METHOCEL ™ K15M Premium CR | 19.55 |
| Avicel ® PH 101 | 14.24 |
| Avicel ® PH 102 | 12.52 |
| METHOCEL ™ E5 Premium LV | 2.04 |
| Talc, USP | 3.00 |
| Colloidal Silicon Dioxide, NF | 1.00 |
| Magnesium Stearate, NF | 1.00 |
| Total | 100 |

The manufacturing process for PD0348-041 differed from PD0348-005 in that the METHOCEL™ E5 was dry blended with the viloxazine hydrochloride, hypromellose (METHOCEL™ K15M) and microcrystalline cellulose (Avicel® PH101) and the EUDRAGIT® NE 30 was sprayed as the granulating fluid.

Figure 4:
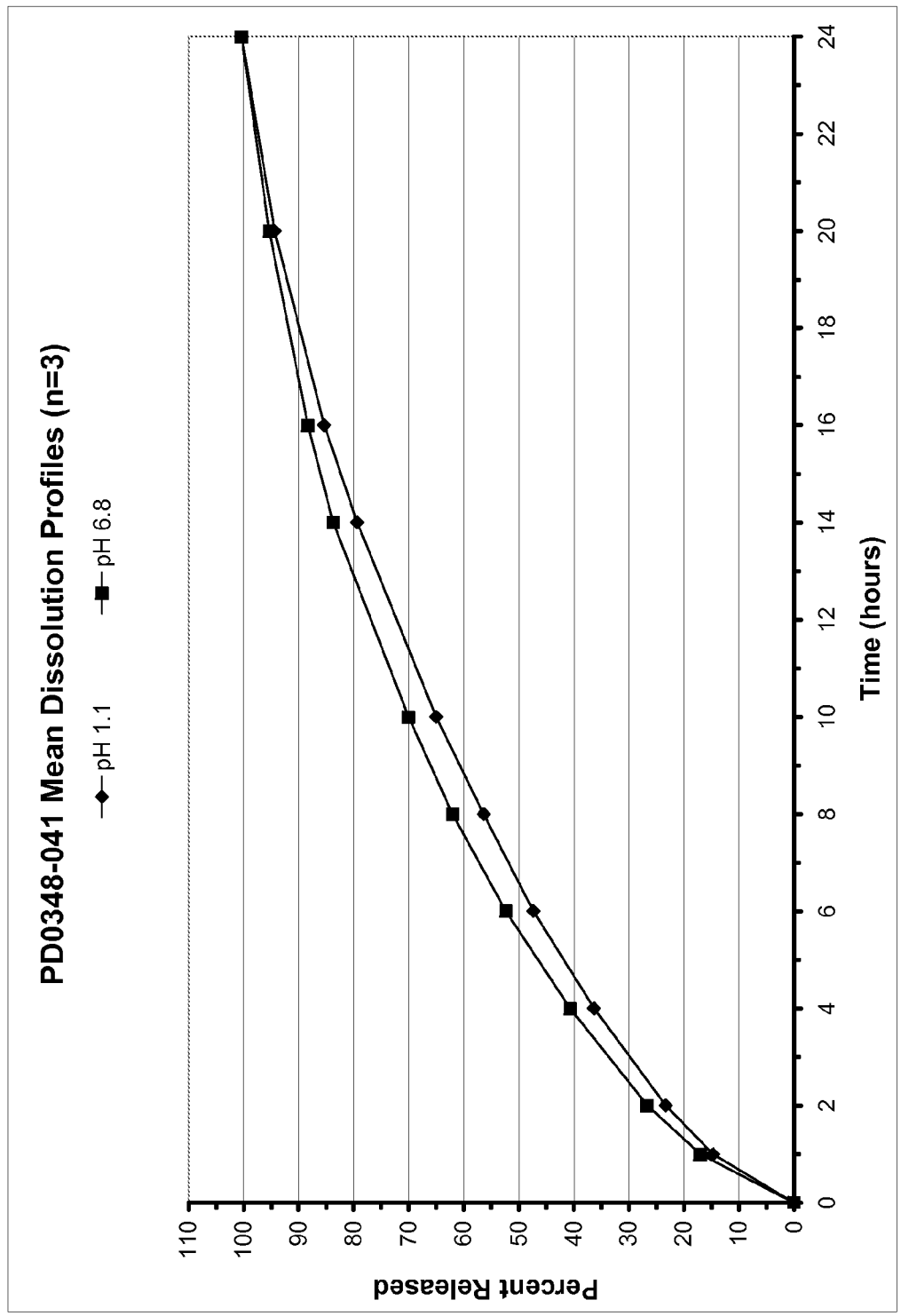
FIG. 4 shows the mean dissolution profiles (n=3) of a 200 mg dose strength tablet (PD0348-041) at pH 1.1 and pH 6.8 (Example 4).

Formulation PD0348-041 was evaluated for drug release by dissolution testing (n=3) at both pH 1.1 and pH 6.8 (FIG. 4). The dissolution profile of PD0348-041 exhibited extended-release with a $t_{80}$ of approximately 14 hours.

Example 5

Pellets of Viloxazine (PD0348-108; PD0348-114A)

Pellets were manufactured using an extrusion/spheronization process to produce high drug load pellets. Initially, a wet granulation was produced (Glatt VG—10 L bowl) comprising viloxazine hydrochloride, microcrystalline cellulose (Avicel® PH101), isomalt (galenIQ™ 810) and talc using a solution of METHOCEL™ E5 in water as the granulating medium. Table 6 provides the granulation formulation.

TABLE 6

Granulation Formulation PD0348-099

| Component | Usage (% w/w) |
| --- | --- |
| Viloxazine Hydrochloride | 75.00 |
| Avicel ® PH 101 | 13.75 |
| galenIQ 810 | 5.25 |
| METHOCEL ™ E5 Premium LV | 3.00 |
| Talc, USP | 3.00 |
| Total | 100 |

The resulting granulation was extruded using a LCI-Fuji Paudal Dome Granulator (Model DG-L2 equipped with a 0.7ϕ/1.0 T screen) and then spheronized using a LCI-Fuji Paudal Marumerizer (Model QJ-400G) to produce IR pellets. The pellets were then oven dried over night at 45° C. The dried pellets were screened (stacked sieves 18 mesh over 40 mesh) and then seal coated using a Wurster process (GPCG-1) to 5% weight gain with Opadry® II White (33G28523) (PVA-based coating system). The seal coated IR pellets, lot PD0348-108, were evaluated for dissolution at pH 1.1 (Table 7). Complete dissolution was observed within 15 minutes.

TABLE 7

Dissolution of 200 mg Dose Strength
IR Pellet Lot PD0348-108 at pH 1.1[a]

| Time (minutes) | Percent Released [b] |
| --- | --- |
| 15 | 98 |
| 30 | 98 |
| 45 | 98 |
| 60 | 98 |
| 120 | 98 |

Figure 5:
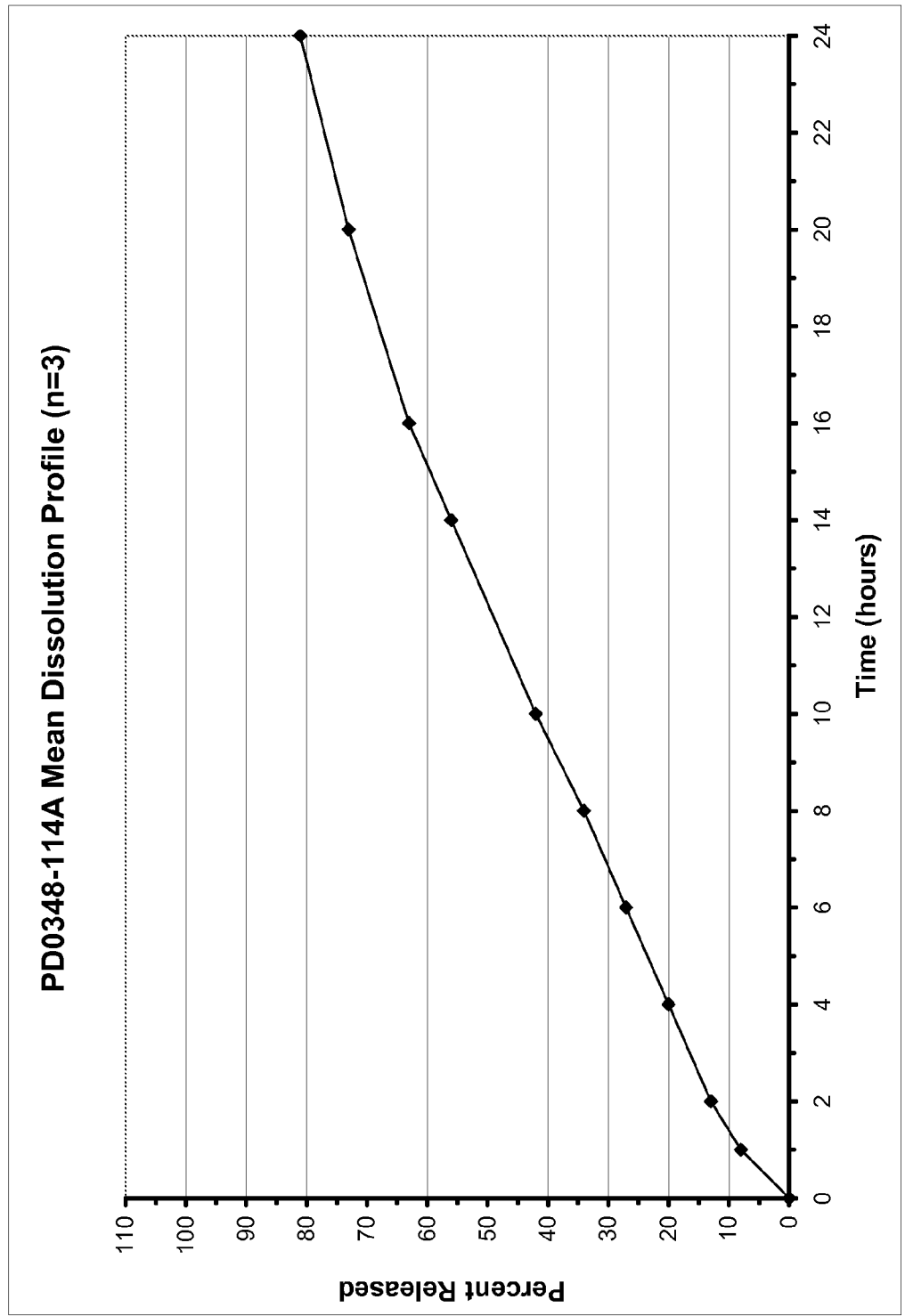
FIG. 5 shows the mean dissolution profile (n=3) of 200 mg dose strength pellets (PD0348-114A) at pH 6.8 (Example 5).

[a]Dissolution conditions: USP II at 50 RPM, 900 mL pH 1.1 0.1N hydrochloric acid at 37° C. (±0.5° C.),
[b]Mean of three vessels The seal coated IR pellets were coated with Surelease® E-7-19010 using a Wurster process (GPCG-1) to a weight gain of 10% (w/w) resulting in viloxazine hydrochloride content in the coated pellets of 64% (w/w) lot PD0348-114A. The coated pellets were oven cured for 72 hours at 50° C. and then evaluated for drug release (FIG. 5). The release profile exhibits near zero order release over the interval of 2 hours to 20 hours ($R^2$ value of 0.997 by linear regression analysis) with a $t_{80}$ of 24 hours. PD0348-114A is an example of a pellet composition exhibiting a slow in vitro release profile that can be combined with one or more pellet compositions having faster release profiles.

Example 6

Multiparticulates of Viloxazine (PD0354-004C)

The granulation formulation (PD0348-134A/B) used to produce the IR pellets for the extended-release pellet lot PD0354-004C is presented in Table 8.

TABLE 8

Granulation Formulation PD0348-134A/B

| Component | Usage (% w/w) |
| --- | --- |
| Viloxazine Hydrochloride | 65.00 |
| Avicel ® PH 101 | 30.00 |
| METHOCEL ™ E5 Premium LV | 1.50 |
| Povidone, USP (K-value 30) | 1.00 |
| Talc, USP | 2.50 |
| Total | 100 |

Figure 6:
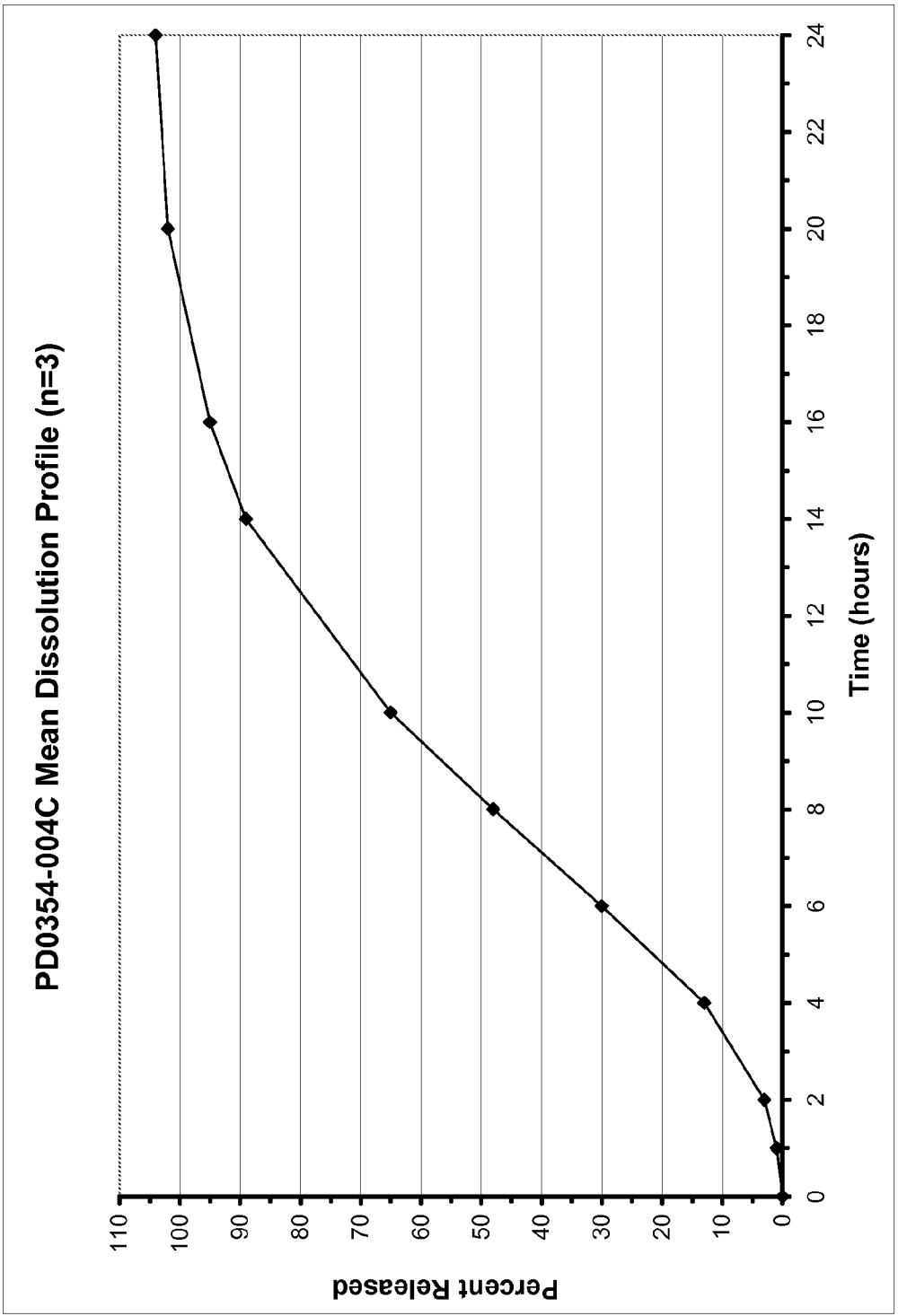
FIG. 6 shows the mean dissolution profile (n=3) of 165 mg dose strength pellets (PD0354-004C) at pH 6.8 (Example 6).

The granulation process for PD0348-134A/B was similar to PD0348-099 with an additional step in that the Povidone, USP was dissolved in the granulating water along with the METHOCEL™ E5. The granulation was extruded on the Model DG-L2 dome granulator equipped with a 0.6ϕ/0.6 T screen and then spheronized on the Model QJ-400G Marumerizer. The spheronized product was oven dried for 24 hours at 45° C. The dried pellets were screened (stacked 20 mesh over 40 mesh sieves) and then seal coated using a Wurster process (GPCG-1) to 5% weight gain with Opadry® II White (33G28523). Following application of the seal coat the pellets were coated with EUDRAGIT® NE 30 D containing Povidone, USP (at a ratio of 9:1 EUDRAGIT® NE 30 D solids to Povidone, USP solids) to a weight gain of 14% (w/w), oven cured for 24 hours at 45° C. and then screened (stacked 20 mesh over 40 mesh sieves). The screened pellets were then coated on the GPCG-1 with Surelease® E-7-19010 to a weight gain of 9% (w/w) resulting in a final viloxazine hydrochloride content of 42% (w/w). The coated pellets were oven cured for 24 hours at 50° C. and then evaluated for drug release (FIG. 6). The release profile exhibits a lag of 1-2 hours and then near zero order release over the interval of 4 hours to 14 hours ($R^2$ value of 0.990 by linear regression analysis) with a $t_{80}$ of 12 hours.

Examples 7, 8 and 9

Extended Release Pellet Formulations

Figure 7:
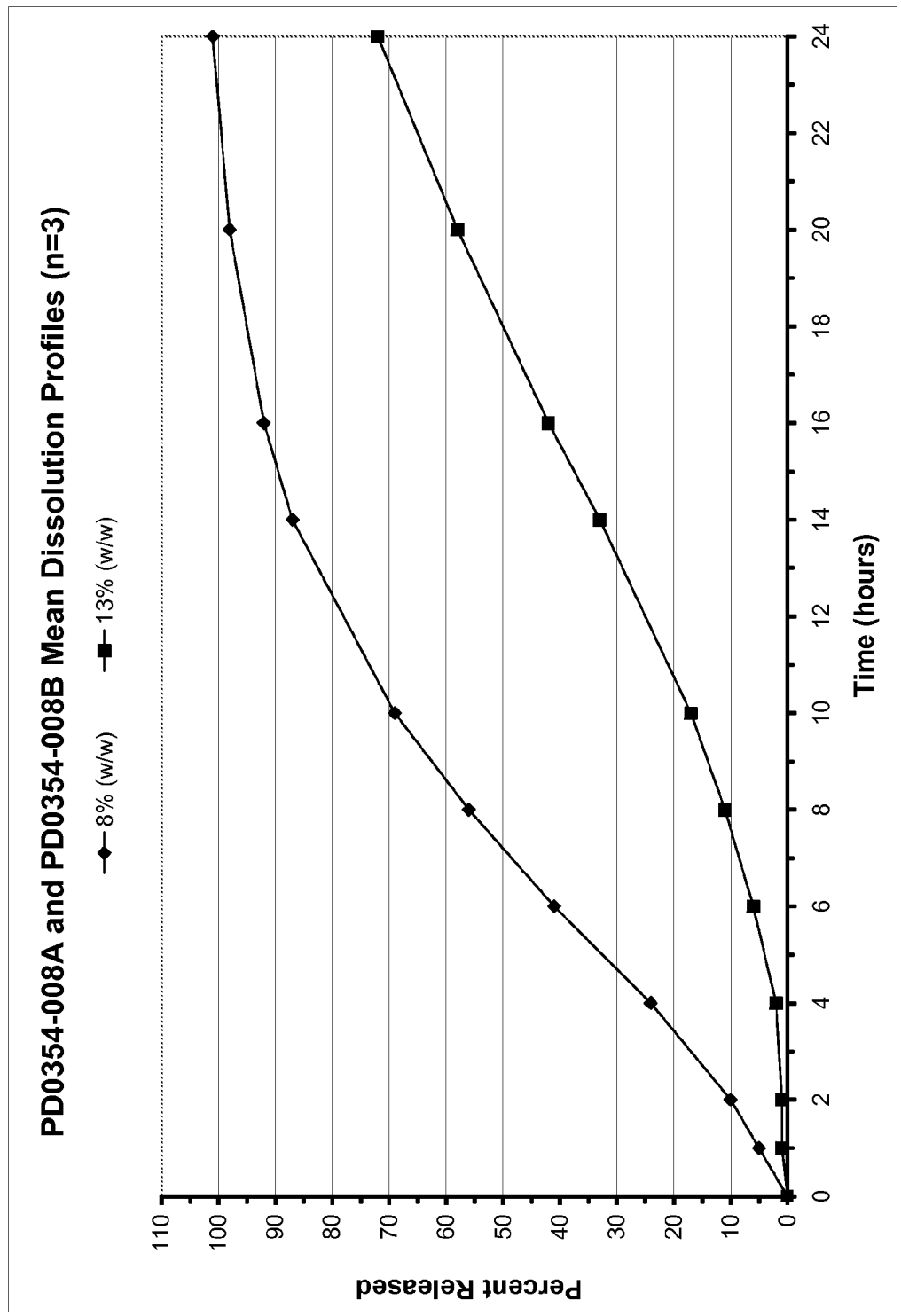
FIG. 7 shows the mean dissolution profiles (n=3) of 200 mg dose strength pellets (PD0354-008A (8% w/w) and PD0354-008B (13% w/w)) at pH 6.8 (Examples 7-9).
Figure 8:
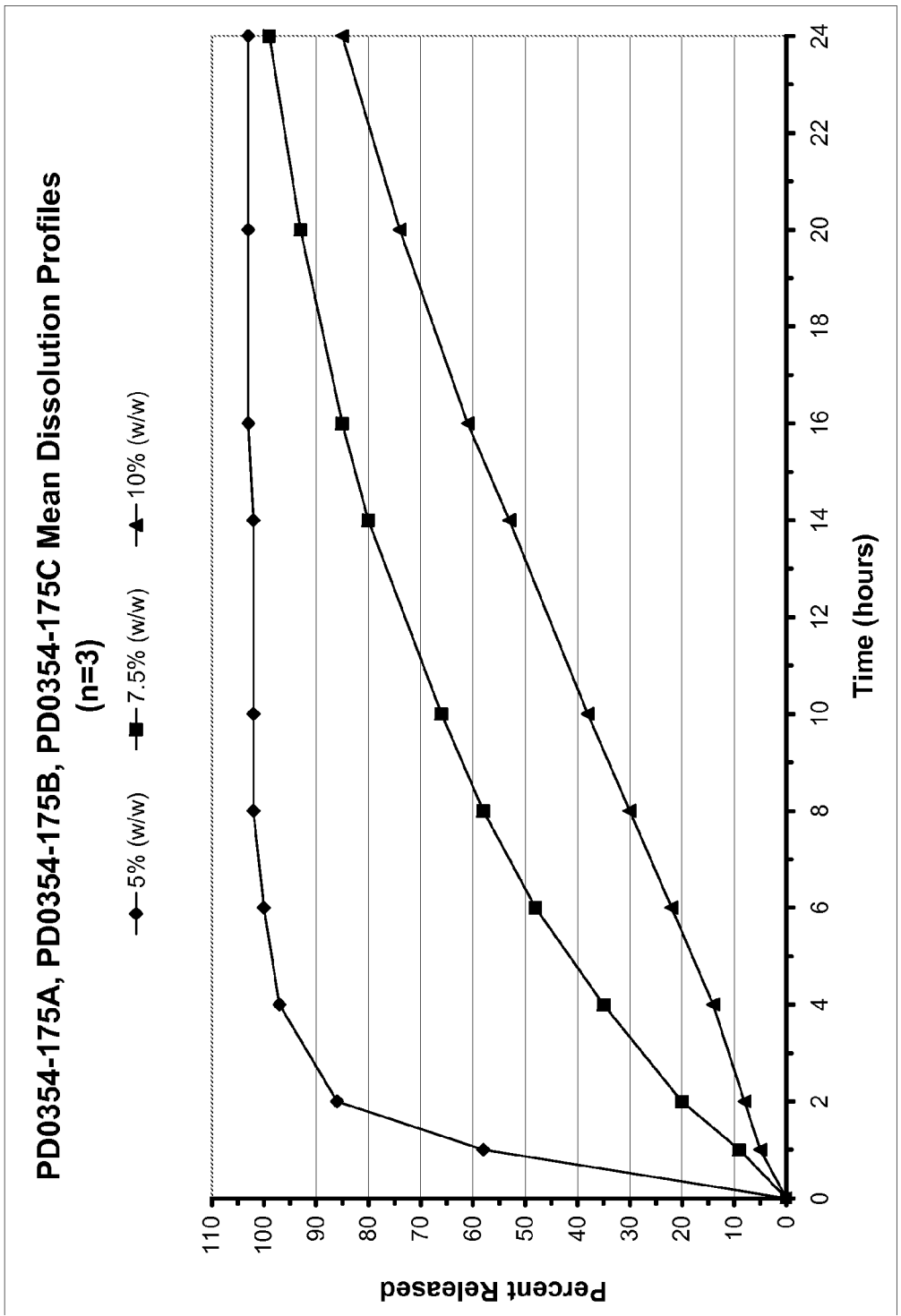
FIG. 8 shows the mean dissolution profiles (n=3) of 200 mg dose strength pellets (PD0354-175A (5% w/w), PD0354-175B (7.5% w/w) and PD0354-175C (10% w/w)) at pH 6.8 (Examples 7-9).
Figure 9:
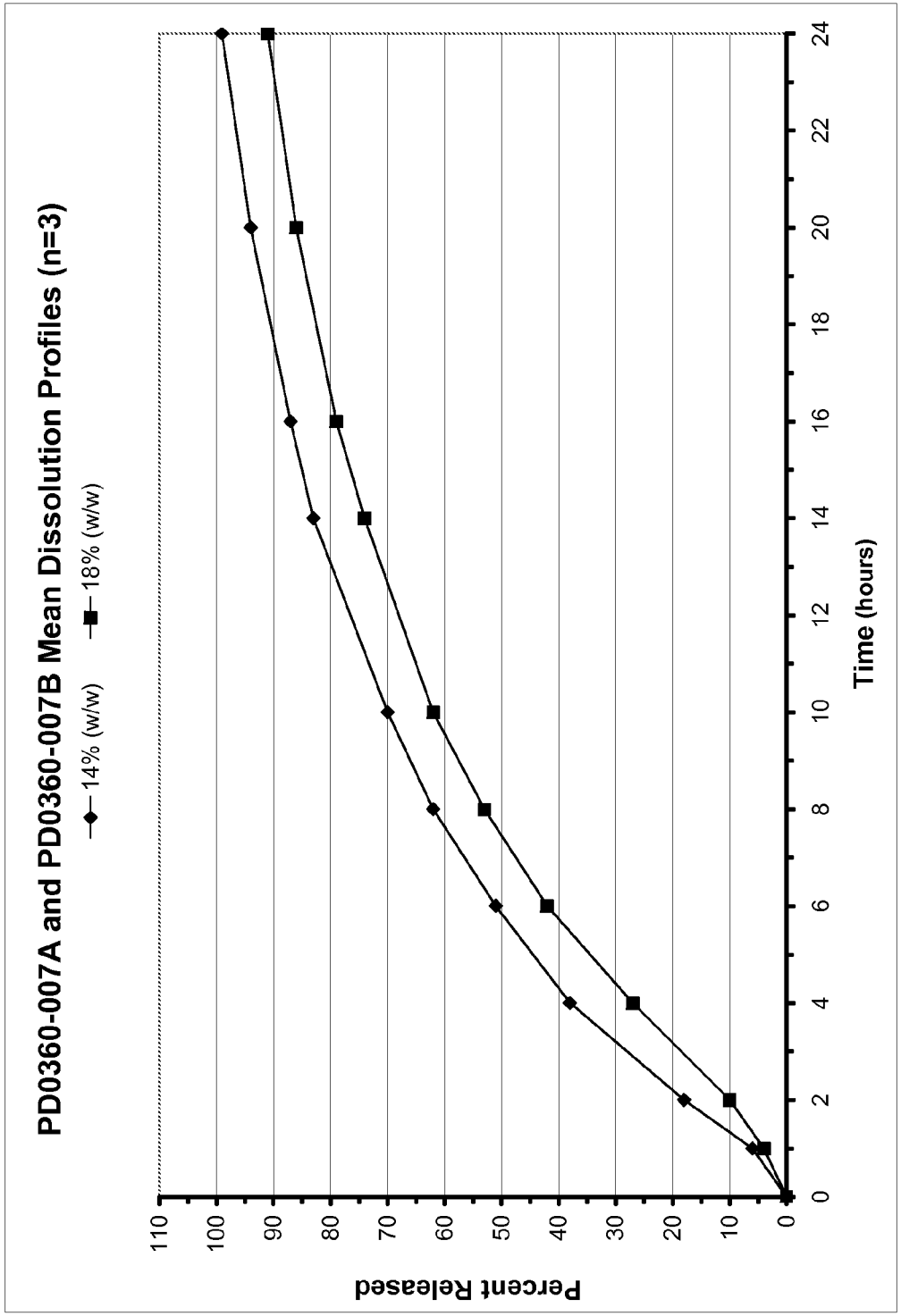
FIG. 9 shows the mean dissolution profiles (n=3) of 200 mg dose strength pellets (PD0360-007A (14% w/w) and PD0360-007B (18% w/w)) at pH 6.8 (Examples 7-9).

A series of extended-release pellet formulations were prepared coating seal coated IR pellets (formulation of Example 6) with Surelease® E-7-19010 containing the pore former, METHOCEL™ E5 Premium LV (E5) to demonstrate the range of extended release profiles that can be achieved with the pellet compositions. The ratios (Surelease® to E5) studied included 19:1, 9:1 and 8.5:1.5. Representative drug release profiles for these systems are presented in FIG. 7 (19:1) for 8% (w/w) and 13% (w/w) coating, FIG. 8 (9:1) for 5% (w/w), 7.5% (w/w) and 10% (w/w) coating, and FIG. 9 (8.5:1.5) for 14% (w/w) and 18% (w/w) coating.

Example 10

Influence of Particle Size on the Drug Release

Figure 10:
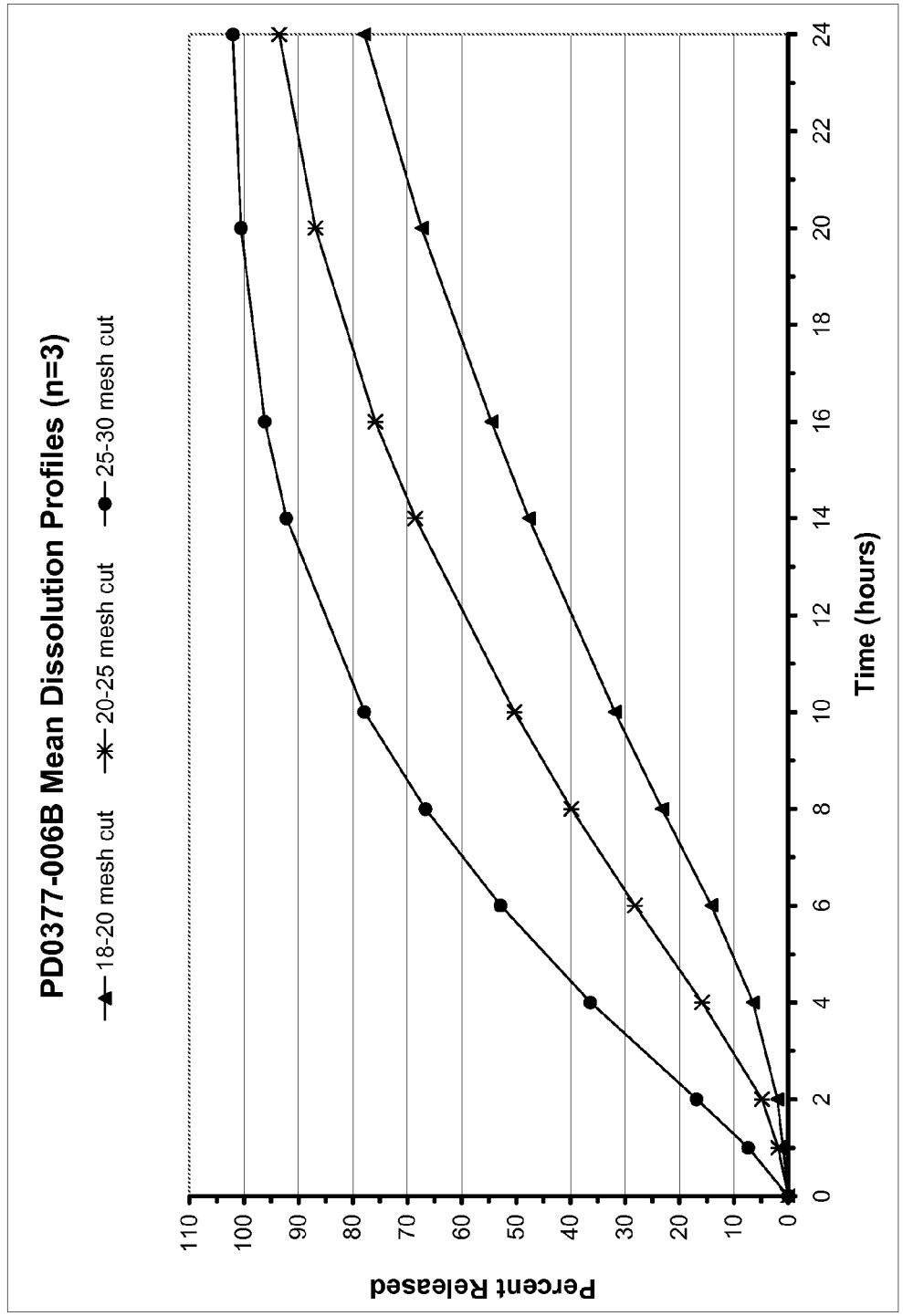
FIG. 10 shows the mean dissolution profiles (n=3) of 200 mg dose strength pellets (PD0377-006B) at pH 6.8 (Example 10).

Studies were conducted to evaluate the drug release from pellets of different particle size fractions, isolated by sieve sizing, after the extended release coating process for lot PD0377-006B. The extended release pellet lot PD0377-006B was prepared by coating seal coated IR pellets (formulation of Example 6) with Surelease® E-7-19010 containing the pore former, METHOCEL™ E5 Premium LV at the ratio of 9:1 to a level of 12% (w/w). The pellet lot was segregated into different size fractions using the following stacked configurations of hand sieves: 18 mesh over 20 mesh, 20 mesh over 25 mesh, and 25 mesh over 30 mesh. Samples of these fractions were evaluated for drug release at pH 6.8 (FIG. 10). The profiles in FIG. 10 illustrate that the size of the IR pellet can be utilized as a controlling parameter for the drug release profile of the pellet formulation. Also, the plots indicate that control of the size distribution of the IR pellets is needed for a robust extended release coating process. The size range for the IR pellets of this invention is 5 mesh (4000 μm) to 200 mesh (75 μm). Ideally the pellet size range is 10 mesh (2000 μm) to 100 mesh (150 μm).

Example 11

Preparation of the Encapsulated Pellets
(PD0380-191, PD0380-192 and PD0383-035

Figure 11:
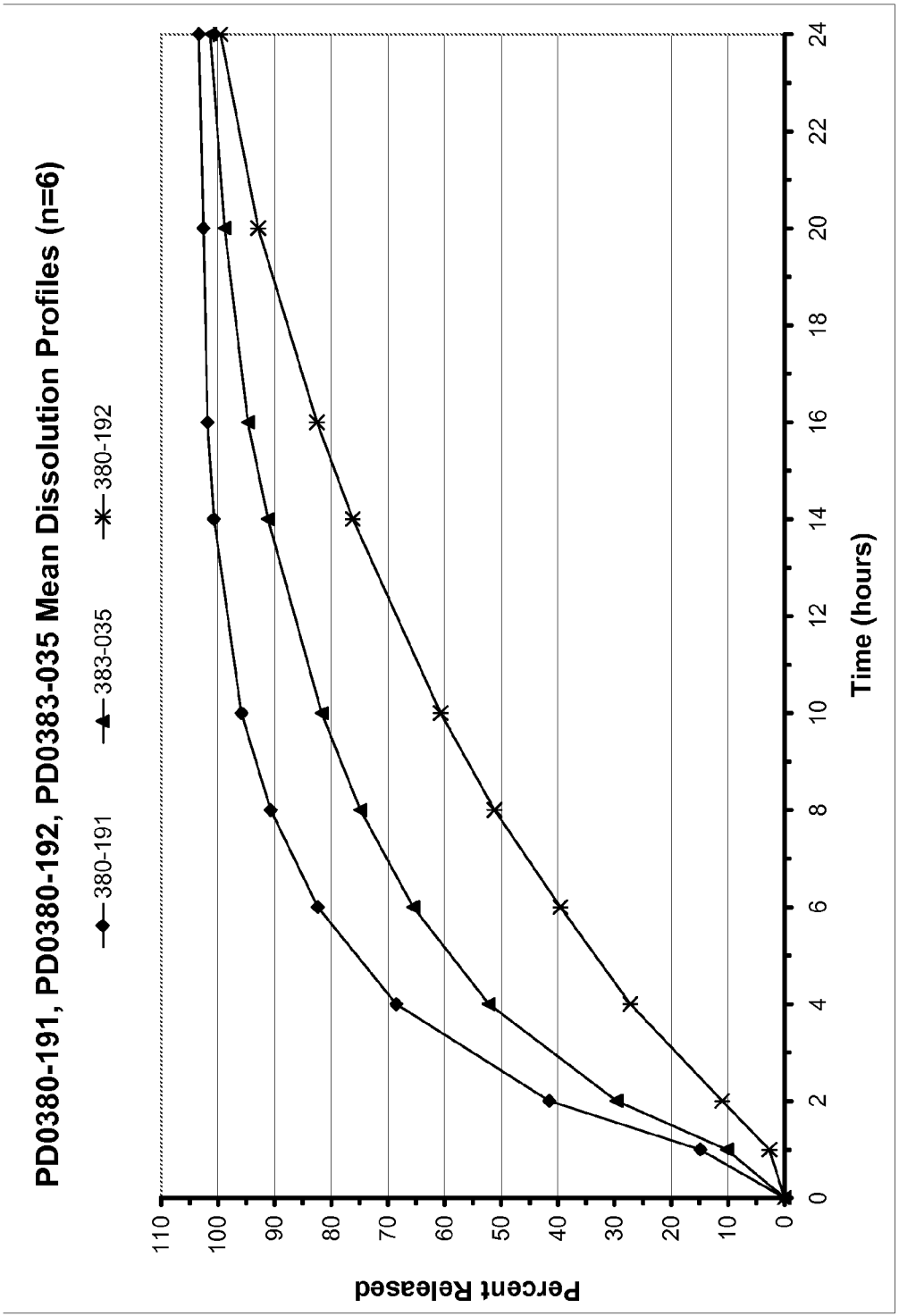
FIG. 11 shows a mean dissolution profiles (n=6) of 150 mg dose strength encapsulated pellets (PD0380-191, PD0383-192 and PD0383-035) at pH 6.8 (Example 11).

Two extended release pellet lots were prepared by coating seal coated IR pellets (formulation of Example 6) with Surelease® E-7-19040 containing the pore former, METHOCEL™ E5 Premium LV at the ratio of 9:1 to a level of 10% (w/w). Extended-release pellet lot PD0380-147B was prepared using seal coated IR pellets of the size fraction between that of a 20 mesh sieve and a 25 mesh sieve. Extended-release pellet lot PD0383-009C was prepared using seal coated IR pellets of the size fraction between that of a 16 mesh sieve and a 20 mesh sieve. The extended-release pellet lots were encapsulated in size 0, white, opaque, hard gelatin capsules at the dose strength of 150 mg viloxazine base; extended-release capsule lot PD0380-191 contained 100% pellet lot PD0380-147B, extended-release capsule lot PD0380-192 contained 100% pellet lot PD0383-009C and extended-release capsule lot PD0383-035 was a mixture of 50% each lot PD0380-147B and lot PD0383-009C. The encapsulated drug products were evaluated for drug release at pH 6.8 (FIG. 11).

Example 12

Influence of the Chloride Ion on the Solubility of Viloxazine Hydrochloride

Figure 12:
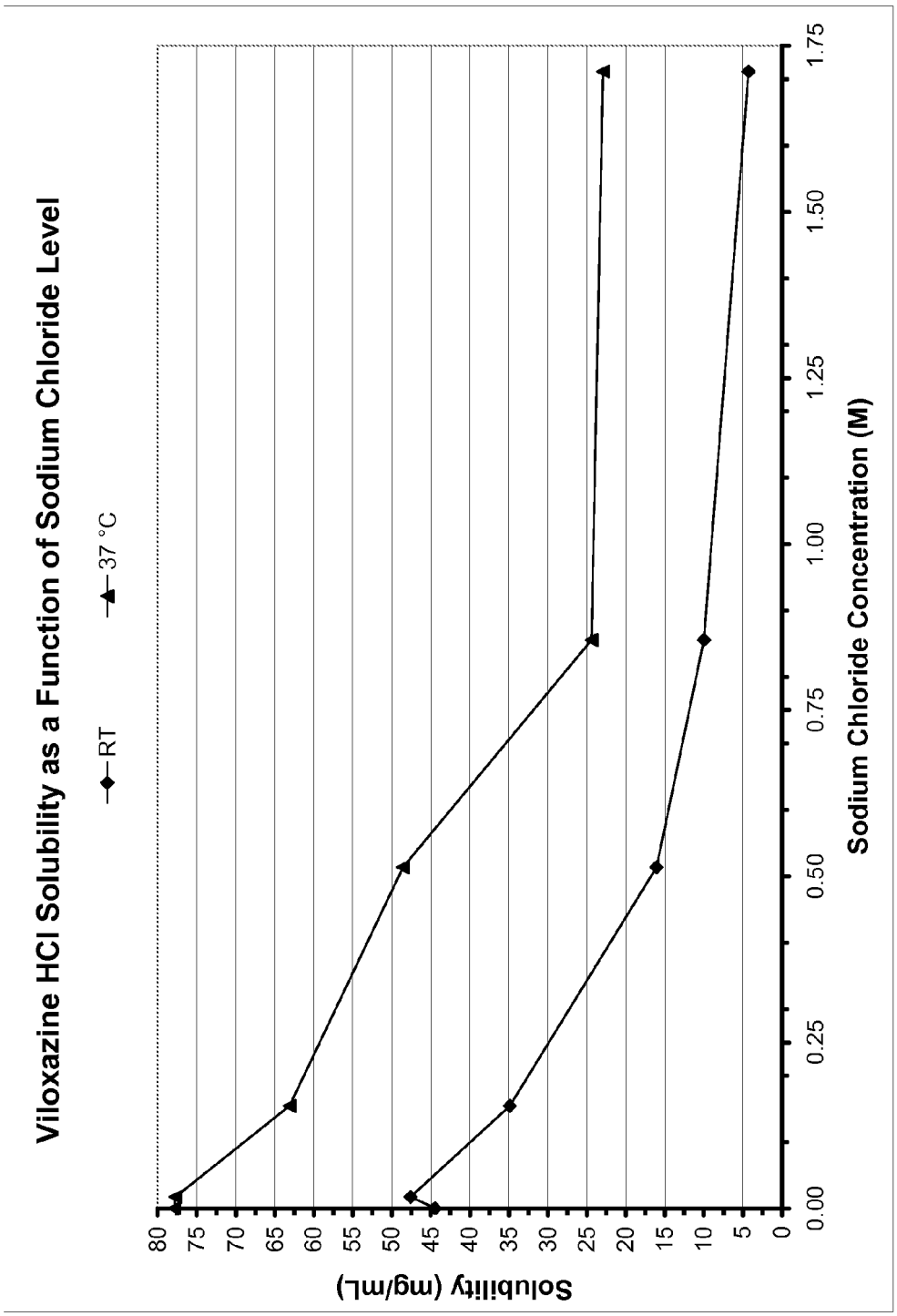
FIG. 12 shows the effect of sodium chloride concentration on the solubility of viloxazine hydrochloride in water at room temperature and 37° C. (Example 12).
Figure 13:
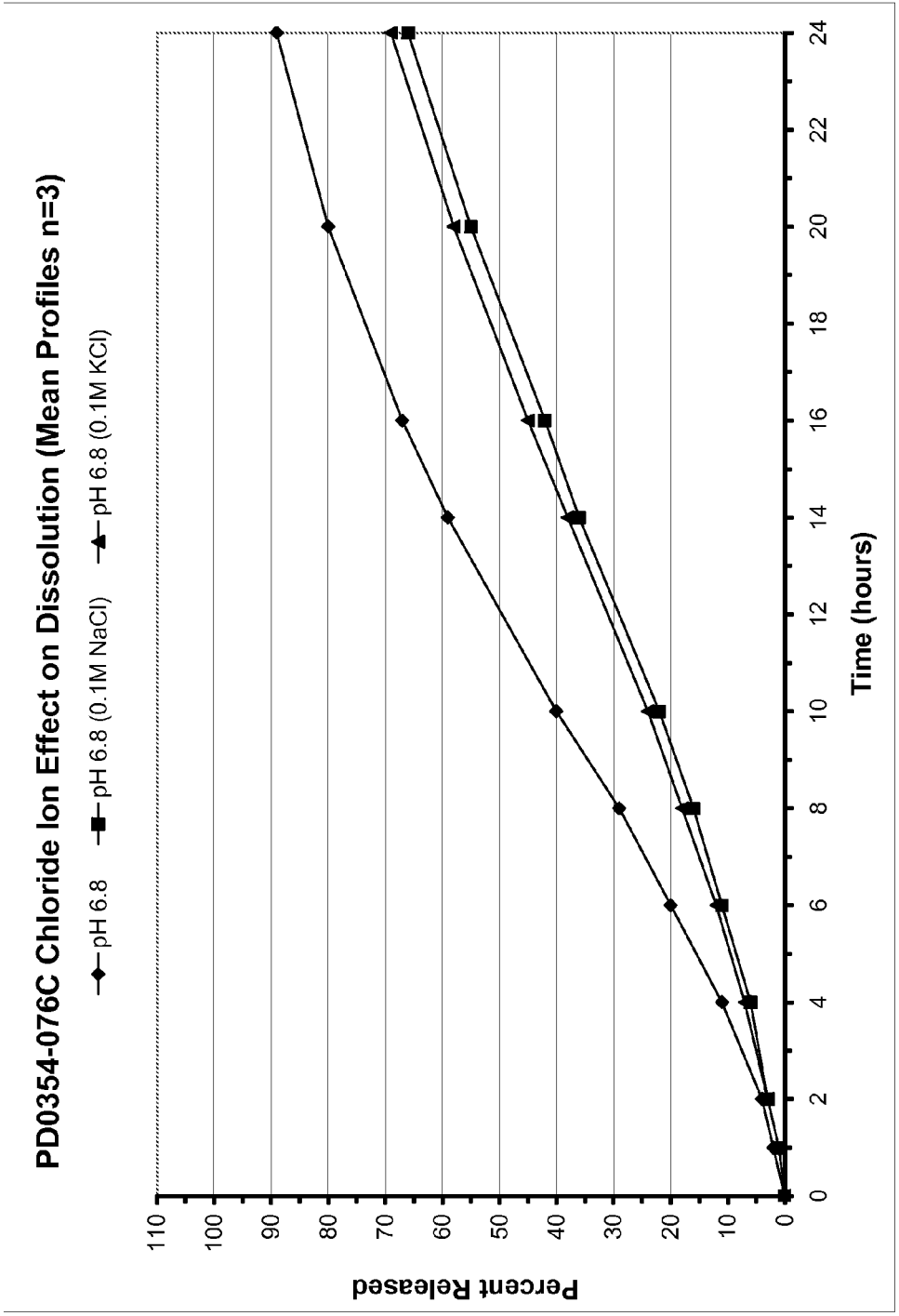
FIG. 13 shows the effect of chloride ion on the mean dissolution profiles (n=3) of 200 mg dose strength pellets (PD0354-076C) at pH 6.8 (Example 12).

It was experimentally determined that the water solubility of viloxazine hydrochloride at room temperature and at 37° C. decreased significantly as a function of sodium chloride concentration (FIG. 12). The reason for the decrease in viloxazine hydrochloride solubility was believed to be a common ion effect of chloride. This effect was further evaluated by adding two chloride ion sources (NaCl and KCl) to pH 6.8 phosphate buffer and evaluating the drug release of pellet formulation PD0354-076C at the dose of 200 mg viloxazine base (231 mg viloxazine hydrochloride) (FIG. 13). The drug release rate was suppressed in both of the media containing the added chloride salts.

Example 13

IR Capsule Formulations of Viloxazine for Clinical Studies

IR capsule formulations of viloxazine developed for use in Phase I and Phase IIa clinical studies (Table 9 and Table 10).

TABLE 9

Viloxazine Capsules, 50 mg (viloxazine base)

| Component | Quantity Per Dosage Unit (g) |
| --- | --- |
| Viloxazine Hydrochloride [a] | 57.68 |
| Microcrystalline Cellulose, NF | 227.84 |
| Magnesium Stearate, NF | 2.88 |
| Hard Gelatin Capsule, Size 0 [b] | 96.0 |
| Total | 384.40 |

[a] Equivalent to 50 mg viloxazine base.
[b] Target empty capsule shell weight based on the product specification.

TABLE 10

Viloxazine Capsules, 100 mg (viloxazine base)

| Component | Quantity Per Dosage Unit (g) |
| --- | --- |
| Viloxazine Hydrochloride [a] | 115.36 |
| Microcrystalline Cellulose, NF | 170.16 |
| Magnesium Stearate, NF | 2.88 |
| Hard Gelatin Capsule, Size 0 [b] | 96.0 |
| Total | 384.40 |

[a] Equivalent to 50 mg viloxazine base.
[b] Target empty capsule shell weight based on the product specification.

Example 14

Extended Release Capsule Formulations of Viloxazine for Clinical Studies

Three extended-release capsule formulations of viloxazine formulated to deliver 150 mg of viloxazine base were developed for a Phase I PK study in healthy subjects. The drug products were formulated to provide different in vitro extended drug release profiles (i.e., fast extended release formulation designated ER-1, medium extended release formulation designated ER-2 and slow extended release formulation designated ER-3). In addition, an immediate-release capsule formulation containing 150 mg of viloxazine base was developed for the clinical study as a comparator drug product.

The manufacture of the extended release drug products started with a wet granulation that was produced utilizing a high-shear granulation process. The wet granulation was extruded and spheronized to form pellets that were subsequently dried by fluid bed resulting in viloxazine nIR pellets (Table 11).

TABLE 11

Viloxazine nIR Pellets (56.36% (w/w) as viloxazine base)

| Component | Quantity Per Batch (g) |
| --- | --- |
| Viloxazine Hydrochloride | 3120.0 |
| Microcrystalline Cellulose, NF | 1440.0 |
| Talc, USP | 120.0 |
| Hypromellose, USP [a] | 72.0 |
| Povidone, USP [b] | 48.0 |
| Sterile Water for Irrigation, USP [c] | 1728.0 |
| Total | 4800 |

[a] Type 2910
[b] K-value 30
[c] Removed during processing

Following drying, the Viloxazine nIR Pellets were screened to produce three specific pellet size ranges based on sieve mesh size: a 25 mesh/35 mesh cut, a 20 mesh/25 mesh cut and a 16 mesh/20 mesh cut. The individual mesh cut Viloxazine nIR Pellets were film coated (Opadry® II White) using a fluid bed producing Viloxazine sIR immediate-release pellets (Viloxazine sIR 2525, Viloxazine sIR 2025 and Viloxazine sIR 1620 pellets). The three Viloxazine sIR Pellet products were used in the production of four extended-release bulk pellets formulations (Viloxazine ER-S Pellets, Viloxazine ER-F Pellets, Viloxazine ER-F2 Pellets and Viloxazine ER-F3 Pellets) by coating the Viloxazine sIR Pellets with an extended-release coating system comprising Surelease® E-7-19040, Hypromellose, USP and Sterile Water for Injection, USP using a fluid bed. The compositions for the four extended release bulk pellets formulations are provided in Tables 12-15.

TABLE 12

Viloxazine ER-S Pellets (47.24% (w/w) as viloxazine base)

| Component | Quantity Per Batch (g) |
|---|---|
| Viloxazine sIR1620 Pellets | 1852.9 |
| Surelease ® E-7-19040 [a, b] | 741.2 |
| Hypromellose, USP [c] | 20.6 |
| Talc, USP | 41.2 |
| Sterile Water for Irrigation, USP [d] | 1166.7 |
| Total | 2100 |

[a] Product number E-7-19040
[b] The quantity for Surelease ® Clear reports the usage of the aqueous coating dispersion.
[c] Type 2910
[d] Removed during processing

TABLE 13

Viloxazine ER-F Pellets (47.24% (w/w) as viloxazine base)

| Component | Quantity Per Batch (g) |
|---|---|
| Viloxazine sIR2025 Pellets | 1852.9 |
| Surelease ® E-7-19040 [a, b] | 741.2 |
| Hypromellose, USP [c] | 20.6 |
| Talc, USP | 41.2 |
| Sterile Water for Irrigation, USP [d] | 1166.7 |
| Total | 2100 |

[a] Product number E-7-19040
[b] The quantity for Surelease ® Clear reports the usage of the aqueous coating dispersion.
[c] Type 2910
[d] Removed during processing

TABLE 14

Viloxazine ER-F2 Pellets (47.24% (w/w) as viloxazine base)

| Component | Quantity Per Batch (g) |
|---|---|
| Viloxazine sIR2535 Pellets | 1852.9 |
| Surelease ® E-7-19040 [a, b] | 741.2 |
| Hypromellose, USP [c] | 20.6 |
| Talc, USP | 41.2 |
| Sterile Water for Irrigation, USP [d] | 1166.7 |
| Total | 2100 |

[a] Product number E-7-19040
[b] The quantity for Surelease ® Clear reports the usage of the aqueous coating dispersion.
[c] Type 2910
[d] Removed during processing

TABLE 15

Viloxazine ER-F3 Pellets (47.24% (w/w) as viloxazine base)

| Component | Quantity Per Batch (g) |
|---|---|
| SPN-812V sIR2535 Pellets (53.54% w/w) | 1852.9 |
| Surelease ® E-7-19040 [a, b] | 741.2 |
| Hypromellose, USP [c] | 20.6 |
| Talc, USP | 41.2 |
| Sterile Water for Irrigation, USP [d] | 1166.7 |
| Total | 2100 |

Figure 14:
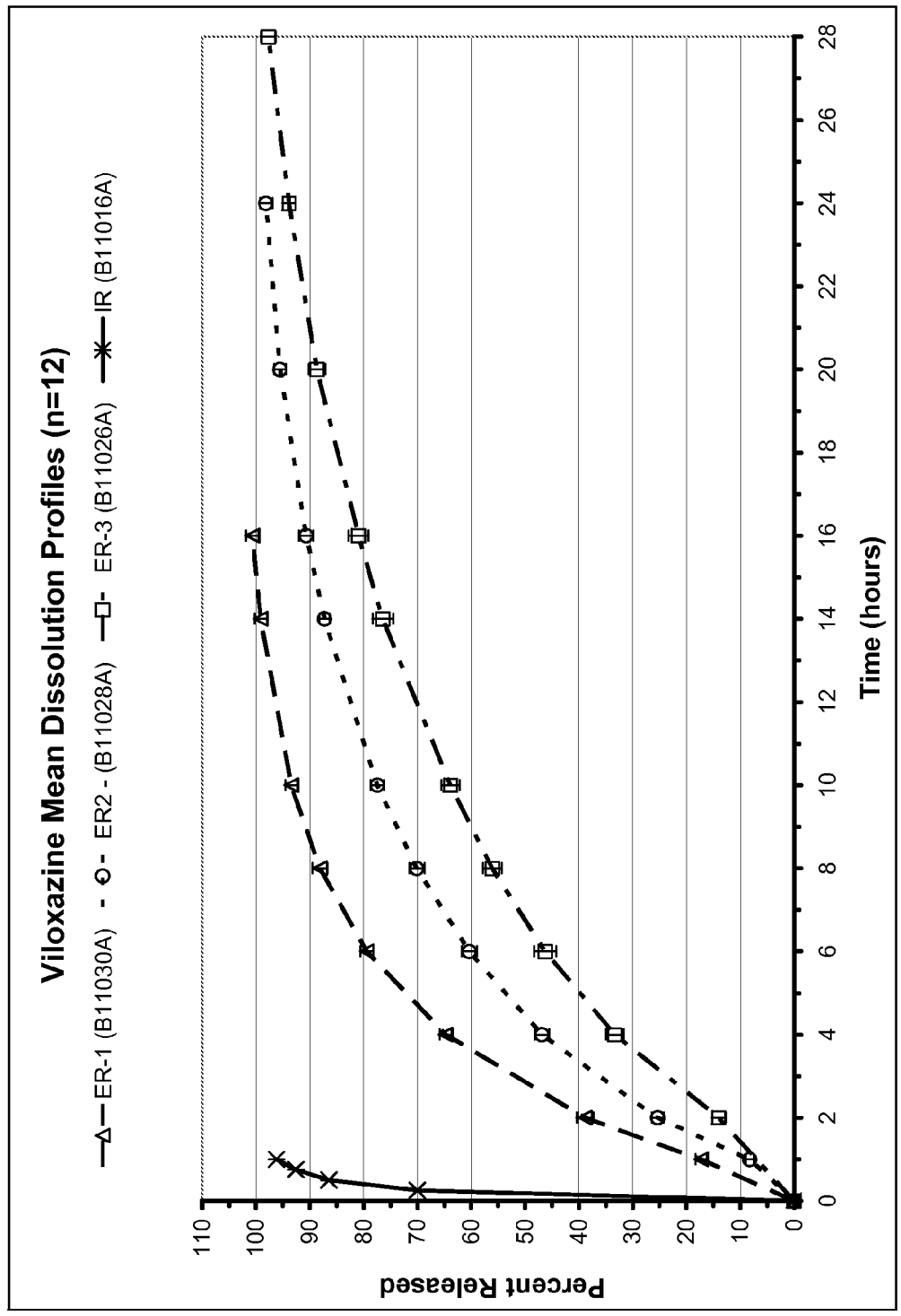
FIG. 14 shows the mean dissolution profiles (n=12) for the IR capsule, ER-1, ER-2 and ER-3 formulations of Example 14.

[a] Product number E-7-19040
[b] The quantity for Surelease ® Clear reports the usage of the aqueous coating dispersion.
[c] Type 2910
[d] Removed during processing Viloxazine sIR2535 Pellets were encapsulated into size 0 white opaque hard gelatin capsules at the dose strength of 150 mg viloxazine base to produce the immediate-release comparator drug product (batch B11016A). Viloxazine ER-F2 Pellets and Viloxazine ER-F3 Pellets were encapsulated, at the ratio of 1:1, into size 0 white opaque hard gelatin capsules at the dose strength of 150 mg viloxazine base to produce Viloxazine ER-1 capsules (batch B11030A). Viloxazine ER-F Pellets were encapsulated into size 0 white opaque hard gelatin capsules at the dose strength of 150 mg viloxazine base to produce Viloxazine ER-2 capsules (batch B11028A). Viloxazine ER-S Pellets were encapsulated into size 0 white opaque hard gelatin capsules at the dose strength of 150 mg viloxazine base to produce Viloxazine ER-3 capsules (batch B11026A). The encapsulated drug products were evaluated for drug release at pH 6.8 (FIG. 14).

Figure 15:
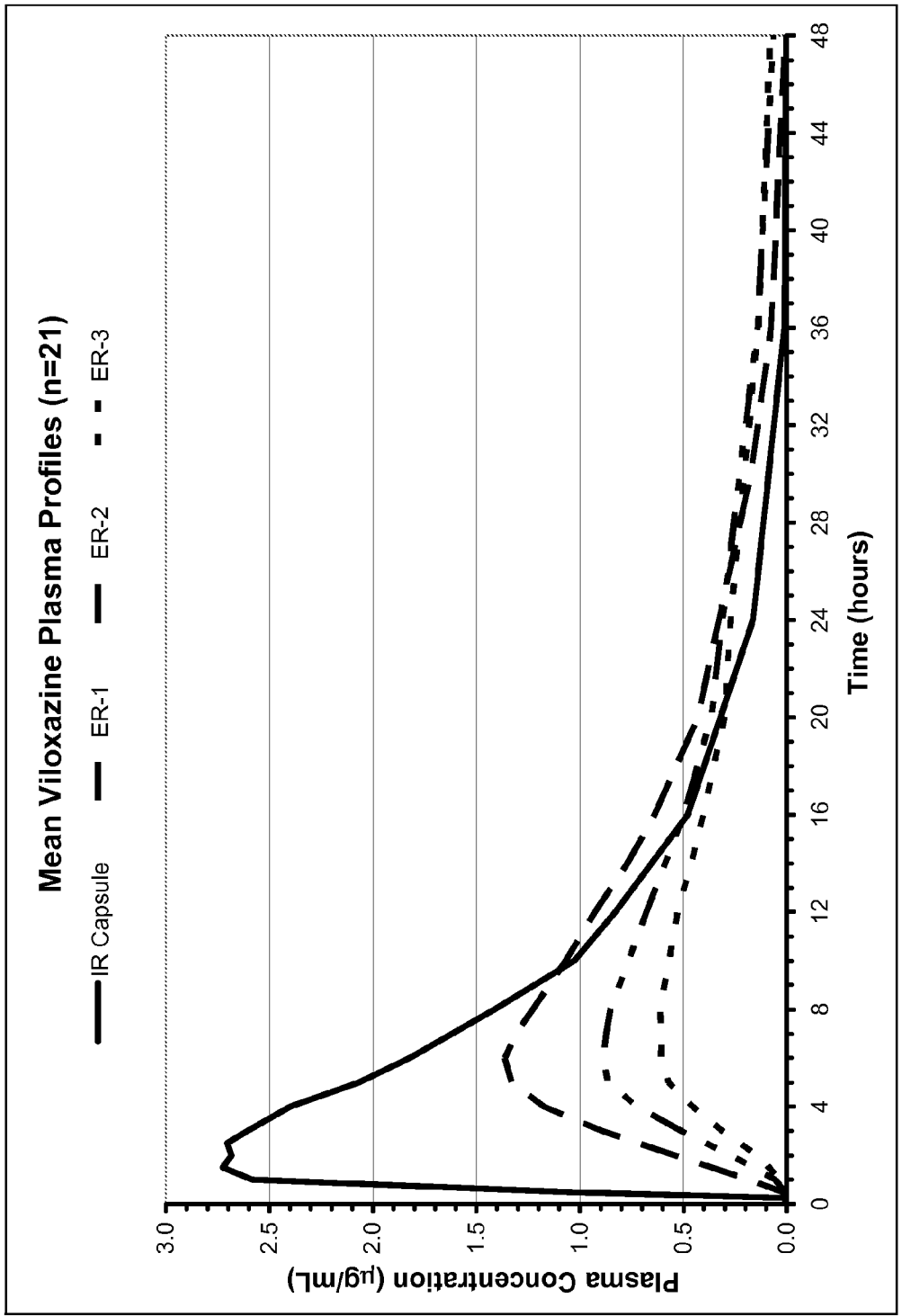
FIG. 15 shows the mean viloxazine plasma profiles obtained in a pilot PK study (n=21 healthy subjects) for the encapsulated IR, ER-1, ER-2 and ER-3 formulations of Example 14.

The pharmacokinetic profile of the three extended-release viloxazine capsule formulations ER-1, ER-2 and ER-3 and the immediate-release capsule formulation was studied in a single dose (150 mg viloxazine base), four treatments, four sequences, crossover study in healthy adult volunteers. Twenty-one subjects completed all four treatment arms. The mean PK profiles from this study are provided in FIG. 15.

Example 15

Pharmacokinetic Analysis of Extended Release Formulations

Non-Compartmental pharmacokinetic analysis was conducted on the mean plasma profiles of Example 14 using WinNonlin Professional version 5.3 (WinNonlin® Copyright© 1998-2009, Tripos L. P.) to determine the percent bioavailability of the three extended-release formulations (ER-1, ER-2 and ER-3) dosed at 150 mg viloxazine base relative to that achieved with the immediate-release capsule formulation also dosed at 150 mg viloxazine base. The percent relative bioavailability values determined were 78% for ER-1, 68% for ER-2 and 57% for ER-3. The relative bioavailability values for the three extended-release formulations were surprising low. The trend in the relative bioavailability values suggests that the absorption of viloxazine is reduced in the distal regions of the gastrointestinal tract and that composite formulation comprising several components with different profiles may be advantageous for maximizing bioavailability.

Example 16

Plasma Profiles of the R- and S-Formulations

Figure 16:
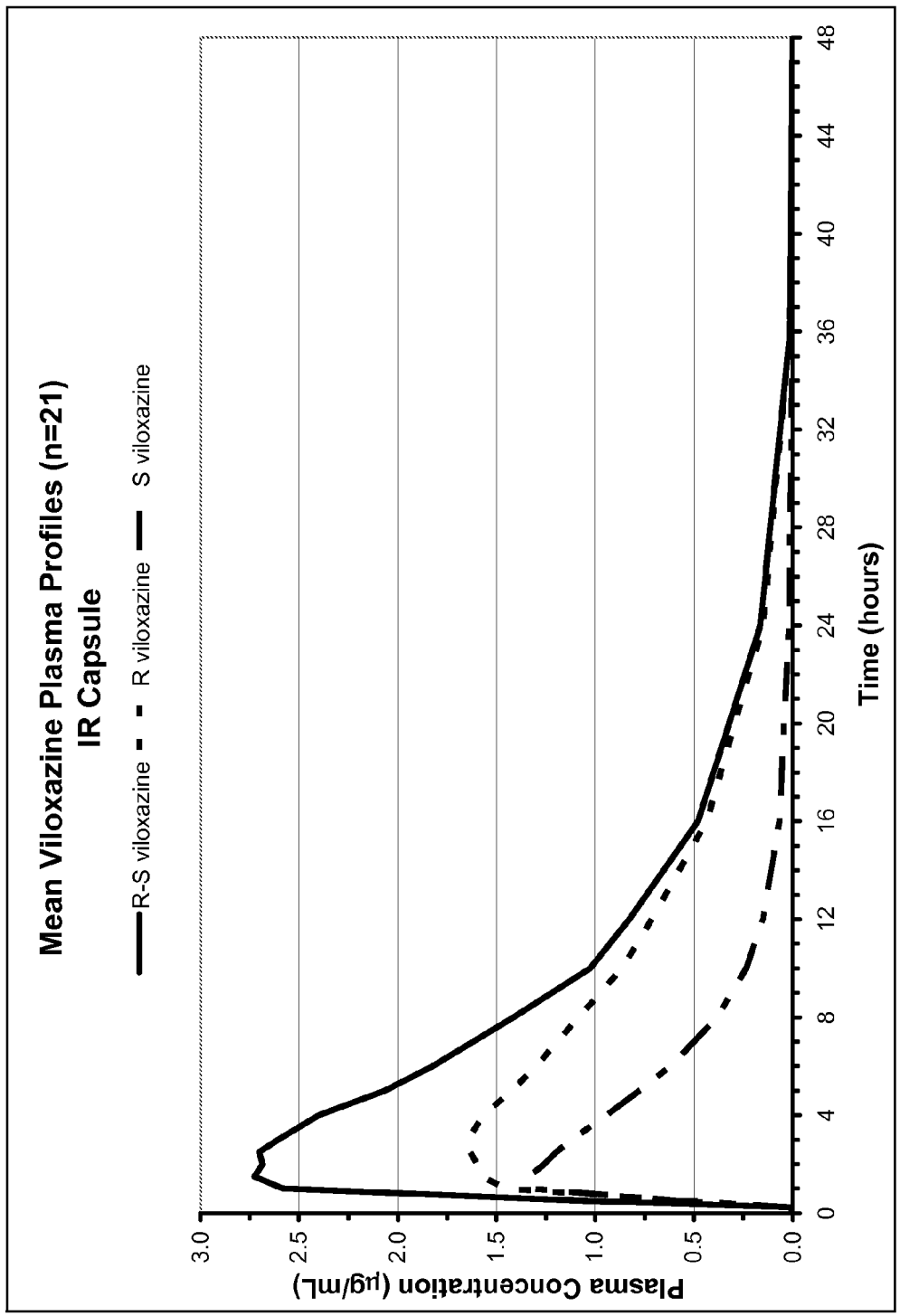
FIG. 16 shows the plasma profiles obtained in a pilot PK study (n=21 healthy subjects) for the IR capsule formulation for RS viloxazine, R-viloxazine and S-viloxazine (Example 16).
Figure 17:
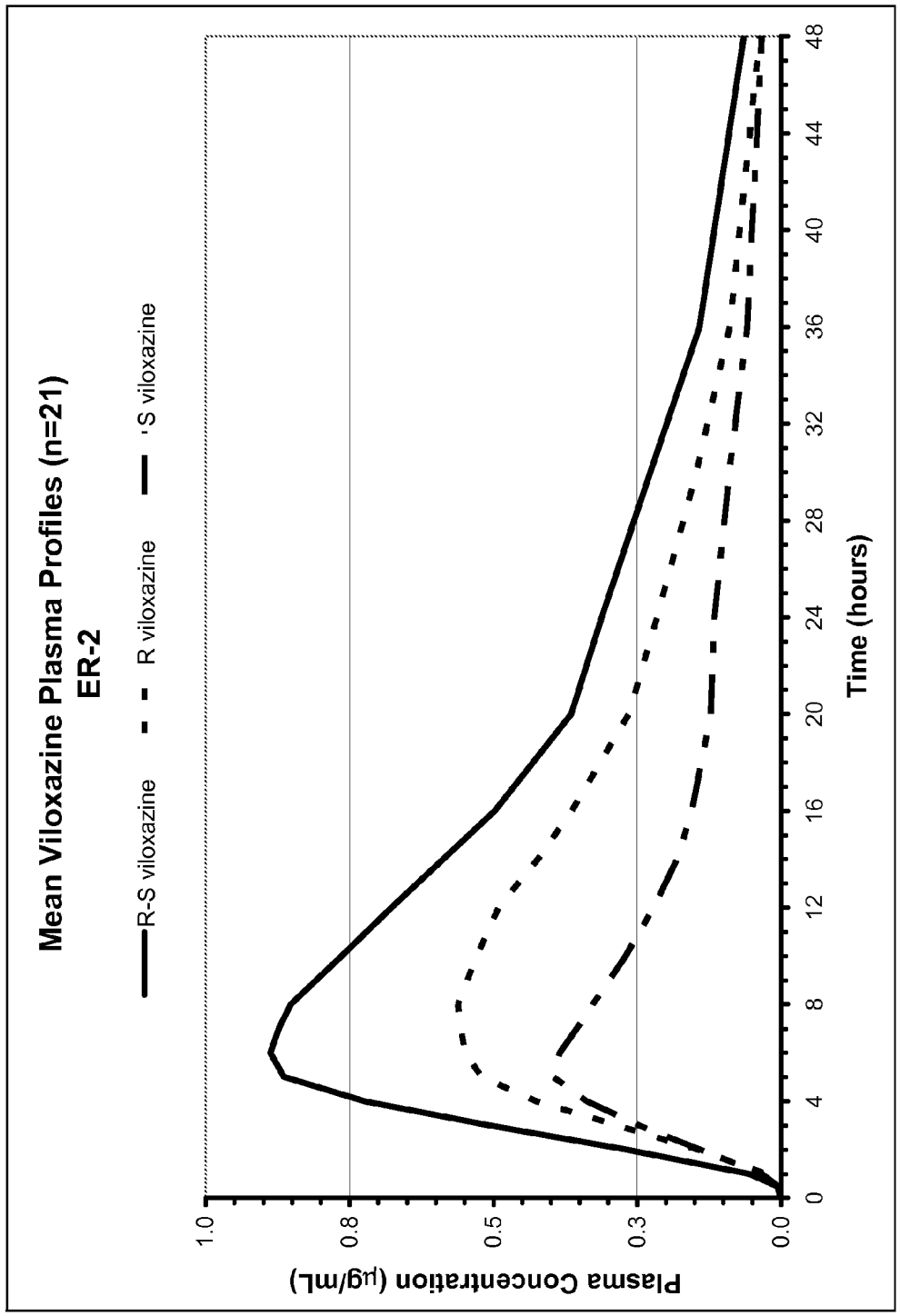
FIG. 17 shows the mean plasma profiles obtained in a pilot PK study (n=21 healthy subjects) for the ER-2 formulation for RS viloxazine, R-viloxazine and S-viloxazine (Example 16).

The plasma samples obtained for the extended-release formulation ER-2 and the IR capsule formulation of Example 14 were evaluated using a bioanalytical method capable of separating R-viloxazine and S-viloxazine. The mean plasma profiles for the individual isomers for the IR capsule formulation are provided in FIG. 16 and the mean plasma profiles for the individual isomers for ER-2 are presented in FIG. 17. The R to S isomer ratio in the actual drug products as well as the drug substance lot used to manufacture the drug products was determined to be 50:50. Surprisingly, the R to S isomer ratio of the mean plasma profiles differed when comparing the IR capsule formulation (70:30) to that of ER-2 (60:40). This finding suggests that R and S isomers may be metabolized differently from the IR and ER formulations and that preferential metabolism of one of the isomers may be induced through strategically developed formulations.

Example 17

In Silico Modeling of the Steady State Viloxazine Systemic In Vivo Exposure (ER1, ER2 and ER3

In silico modeling was conducted using GastroPlus™ (copyright 2001-2010 Simulations Plus Inc.) and the mean drug release and plasma concentration profiles of Example 14 to develop simulated plasma concentration profiles for extended-release formulation concepts exhibiting steady state viloxazine systemic in vivo exposure similar to that of immediate-release formulation dosing schemes. All formulation doses used were as viloxazine base.

Figure 18:
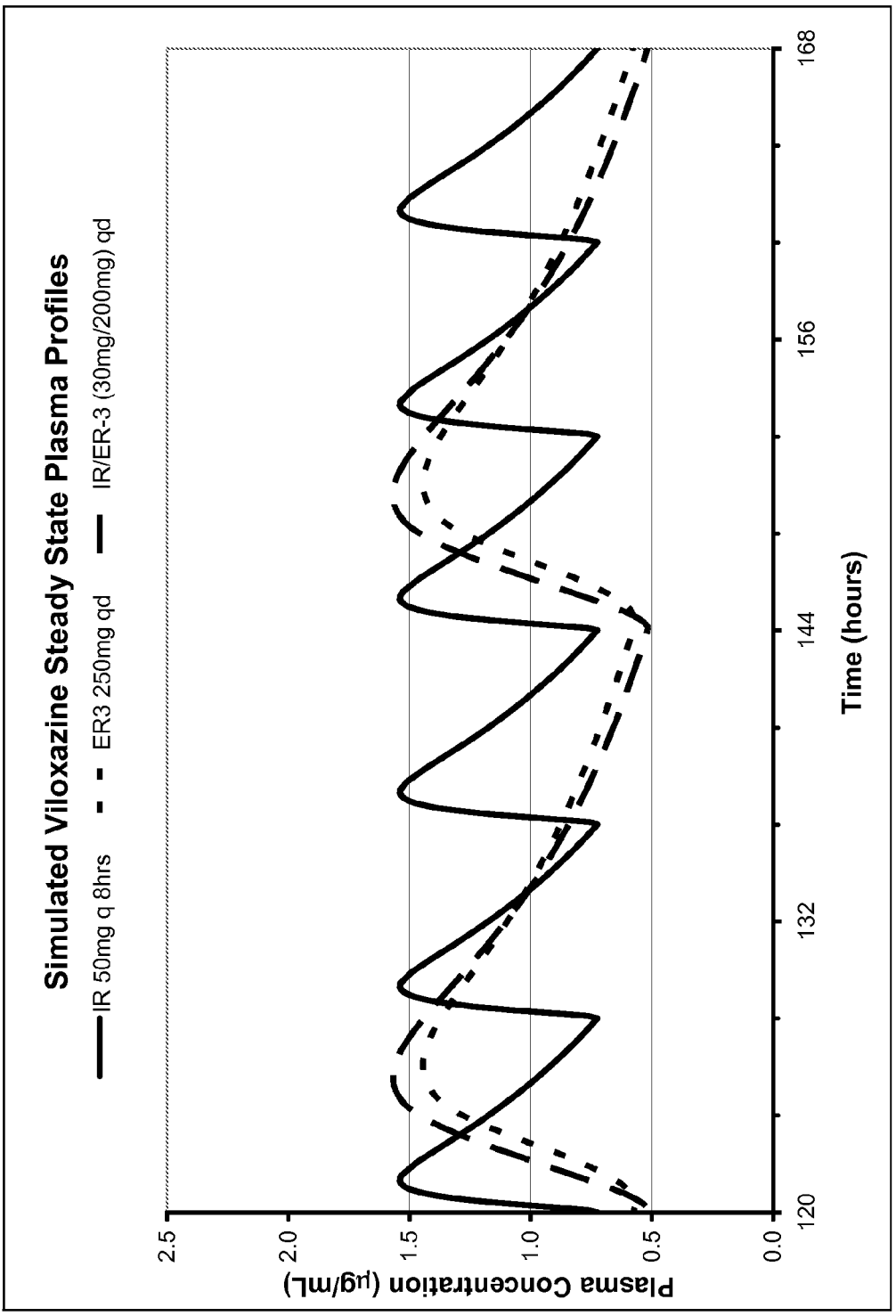
FIG. 18 shows simulated viloxazine steady state plasma profiles comparing an IR formulation dosed 50 mg every 8 hours daily, to the extended-release compositions of Example 17(a).

(a) FIG. 18 presents the comparison of the steady state simulated plasma profiles for an immediate-release 50 mg viloxazine dosage form dosed every 8 hours (TID) to that of two extended-release viloxazine formulation compositions dosed once daily (qd). The first extended release composition contains 250 mg of ER-3 pellets and the second extended release composition contains 30 mg IR pellets and 200 mg of ER-3 pellets. Pharmacokinetic analysis of the simulated profiles for a dosing cycle of 24 hours ($AUC_{tau}$) estimated that the systemic in vivo exposure for the extended-release composition of 250 mg ER-3 pellets would be 86% and that for the composition of 30 mg IR pellets and 200 mg of ER-3 pellets would be 89% of the systemic exposure achieved with this particular IR dosing scheme.

Figure 19:
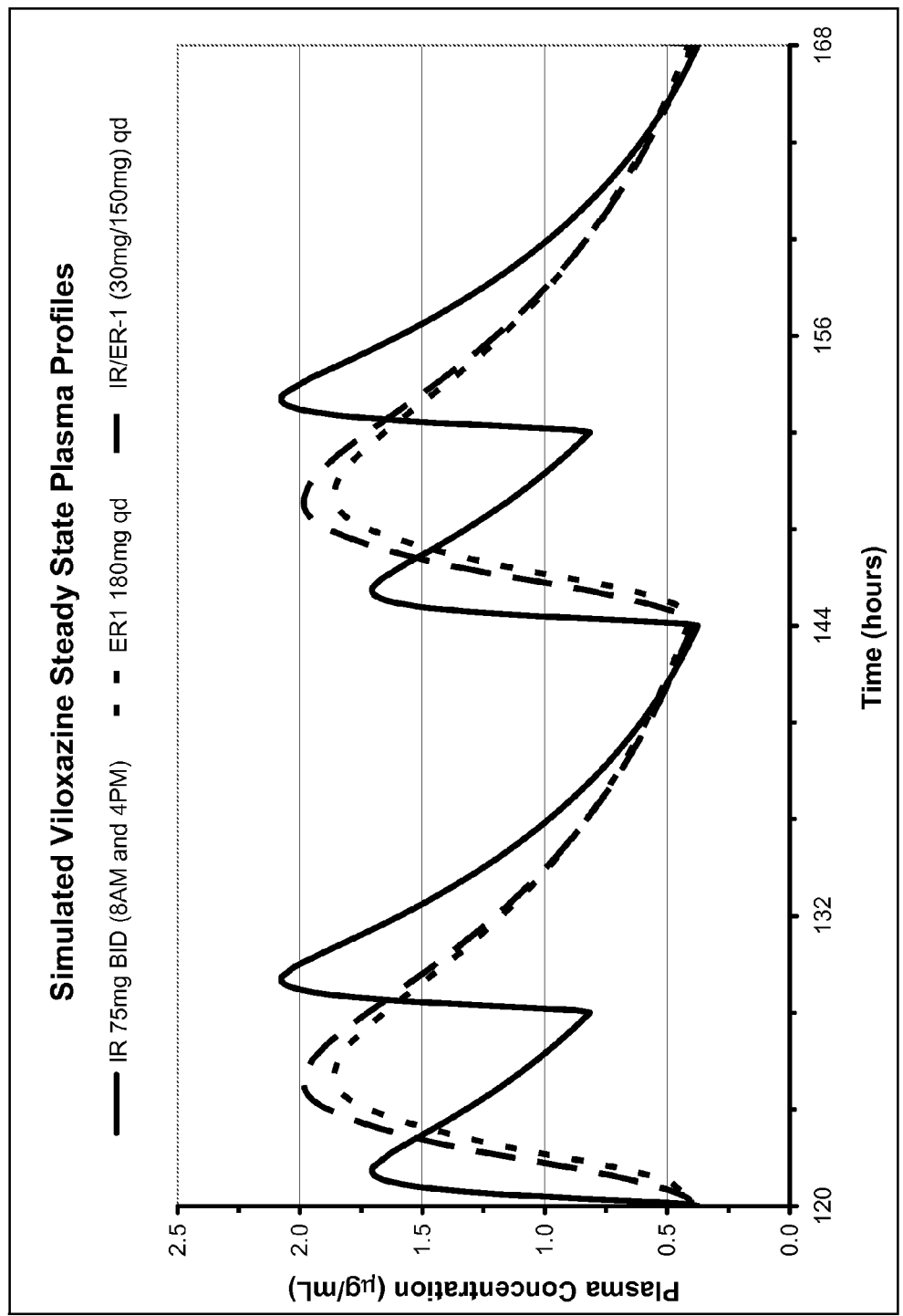
FIG. 19 shows simulated viloxazine steady state plasma profiles comparing an IR formulation dosed 75 mg twice daily (8 hours apart), to the extended-release compositions of Example 17 (b).
Figure 20:
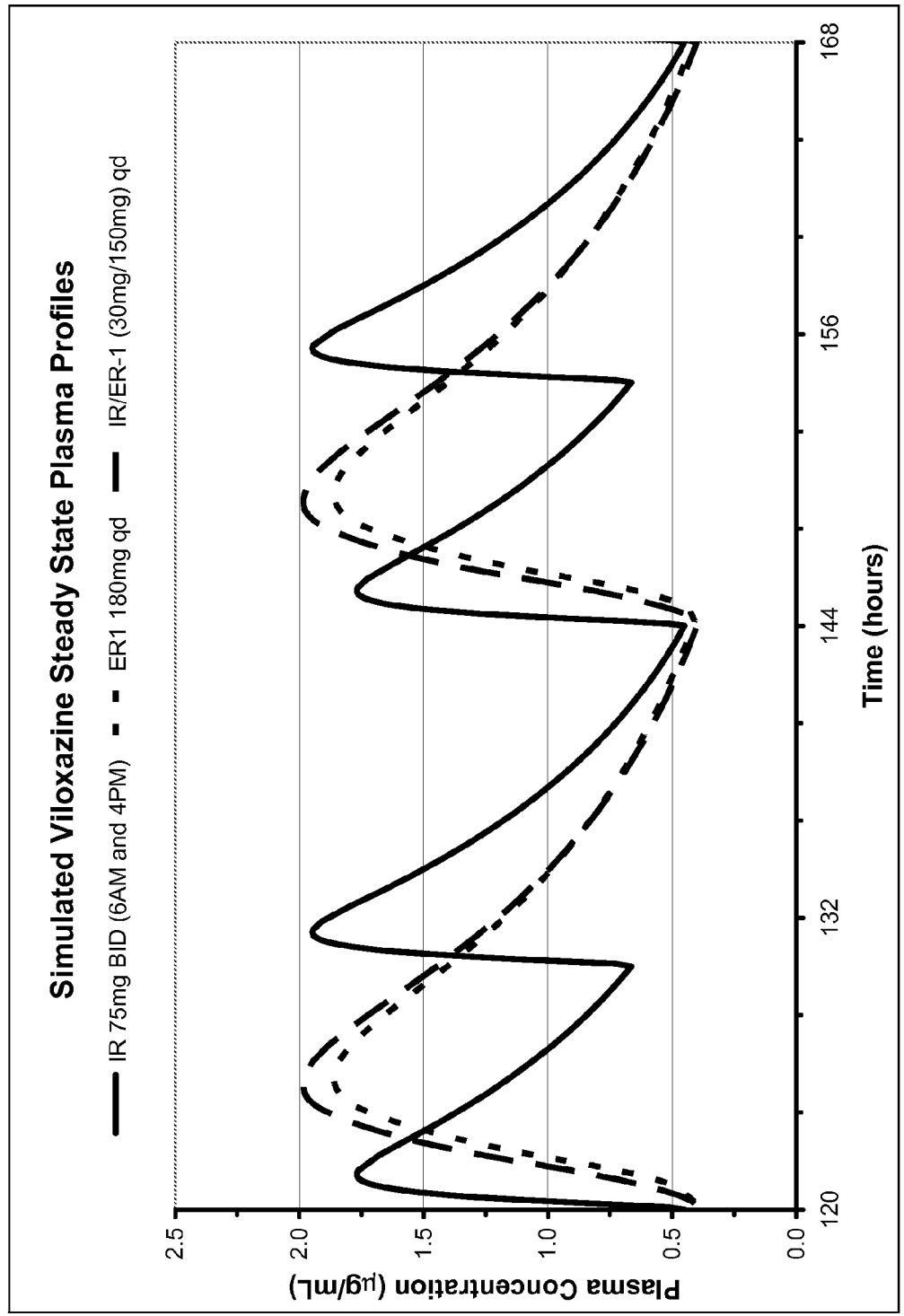
FIG. 20 shows simulated viloxazine steady state plasma profiles comparing an IR formulation dosed 75 mg twice daily (10 hours apart), to the extended-release compositions of Example 17(b).

(b) FIG. 19 presents the comparison of the steady state simulated plasma profiles for an immediate-release 75 mg viloxazine dosage form dosed twice daily (BID) with the first dose given at 8 AM and the second dose given 8 hours later (at 4 PM) to that of two extended-release viloxazine formulation compositions dosed qd. The first extended release composition contains 180 mg of ER-1 pellets and the second extended release composition contains 30 mg IR pellets and 150 mg of ER-1 pellets. Pharmacokinetic analysis of the simulated profiles for a dosing cycle of 24 hours ($AUC_{tau}$) estimated that the systemic in vivo exposure for the extended-release composition of 180 mg ER-1 pellets would be 93% and that for the composition of 30 mg IR pellets and 150 mg of ER-1 pellets would be 98% of the systemic exposure achieved with this IR dosing scheme. FIG. 20 presents the same extended-release compositions however, compared to an IR BID dosing scheme with the first dose given at 6 AM and the second dose given at 4 PM (10 hours later). The first extended release composition contains 180 mg of ER-1 pellets and the second extended release composition contains 30 mg IR pellets and 150 mg of ER-1 pellets.

Figure 21:
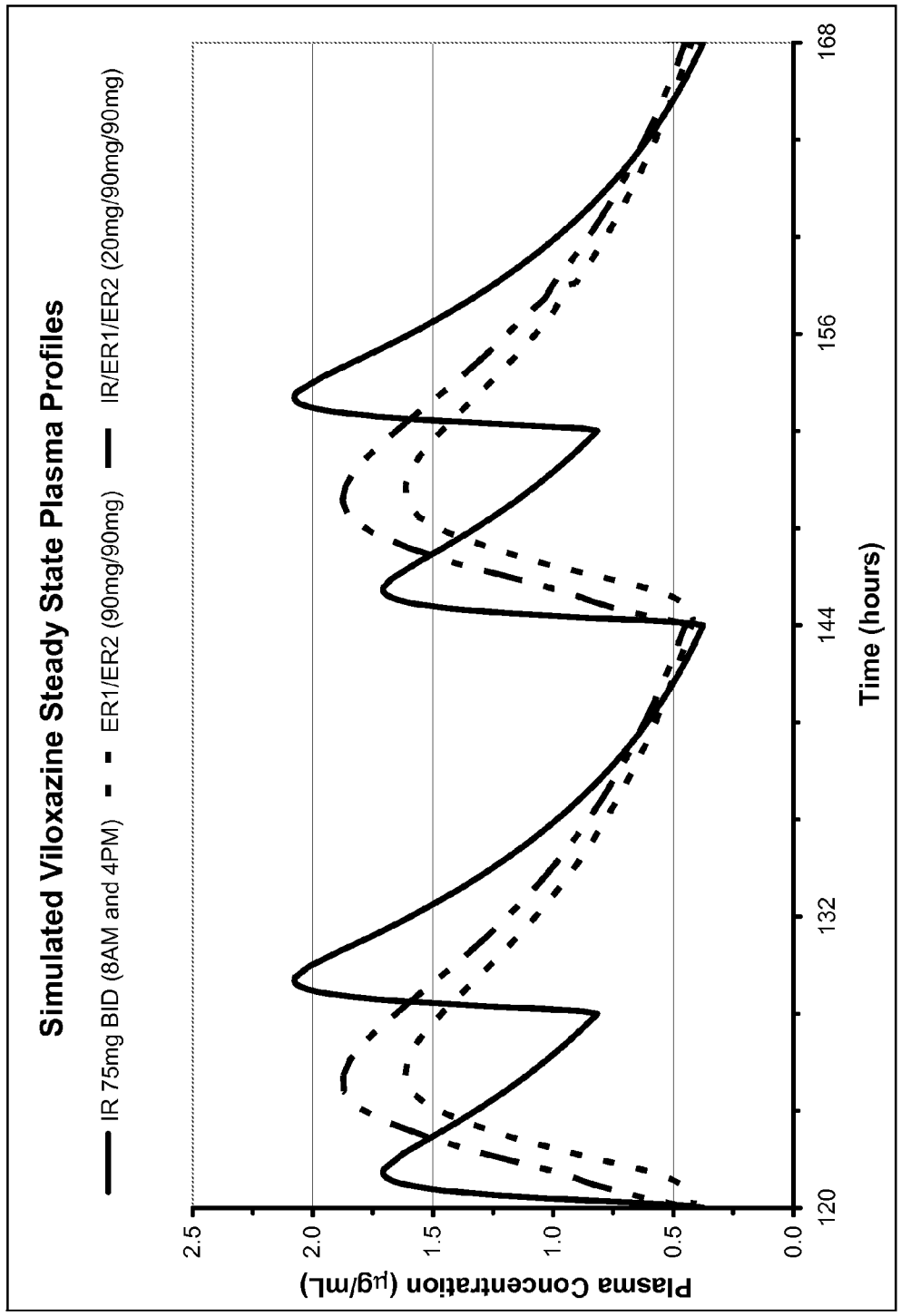
FIG. 21 shows simulated viloxazine steady state plasma profiles comparing an IR formulation dosed 75 mg twice daily (8 hours apart), to the extended-release compositions of Example 17(c).

(c) FIG. 21 presents the comparison of the steady state simulated plasma profiles for an immediate-release 75 mg viloxazine dosage form dosed twice daily (BID) with the first dose given at 8 AM and the second dose given 8 hours later (at 4 PM) to that of two extended-release viloxazine formulation compositions dosed qd. The first extended release composition contains 90 mg of ER-1 pellets and 90 mg of ER-2 pellets. The second extended release composition contains 20 mg IR pellets, 90 mg of ER-1 pellets and 90 mg of ER-2 pellets. Pharmacokinetic analysis of the simulated profiles for a dosing cycle of 24 hours ($AUC_{tau}$) estimated that the systemic in vivo exposure for the extended-release composition of 90 mg of ER-1 pellets and 90 mg of ER-2 pellets would be 85% and that for the composition of 20 mg immediate-release pellets, 90 mg of ER-1 pellets and 90 mg of ER-2 pellets would be 98% of the systemic exposure achieved with this IR dosing scheme.

Example 18

In Silico Modeling of the Steady State Viloxazine Systemic In Vivo Exposure of ER Capsule Composition In silico modeling was conducted using GastroPlus™ (copyright 2001-2010 Simulations Plus Inc.) to develop a simulated plasma concentration profile for a three pellet extended release capsule composition concept. All formulation doses used were as viloxazine base.

Figure 22:
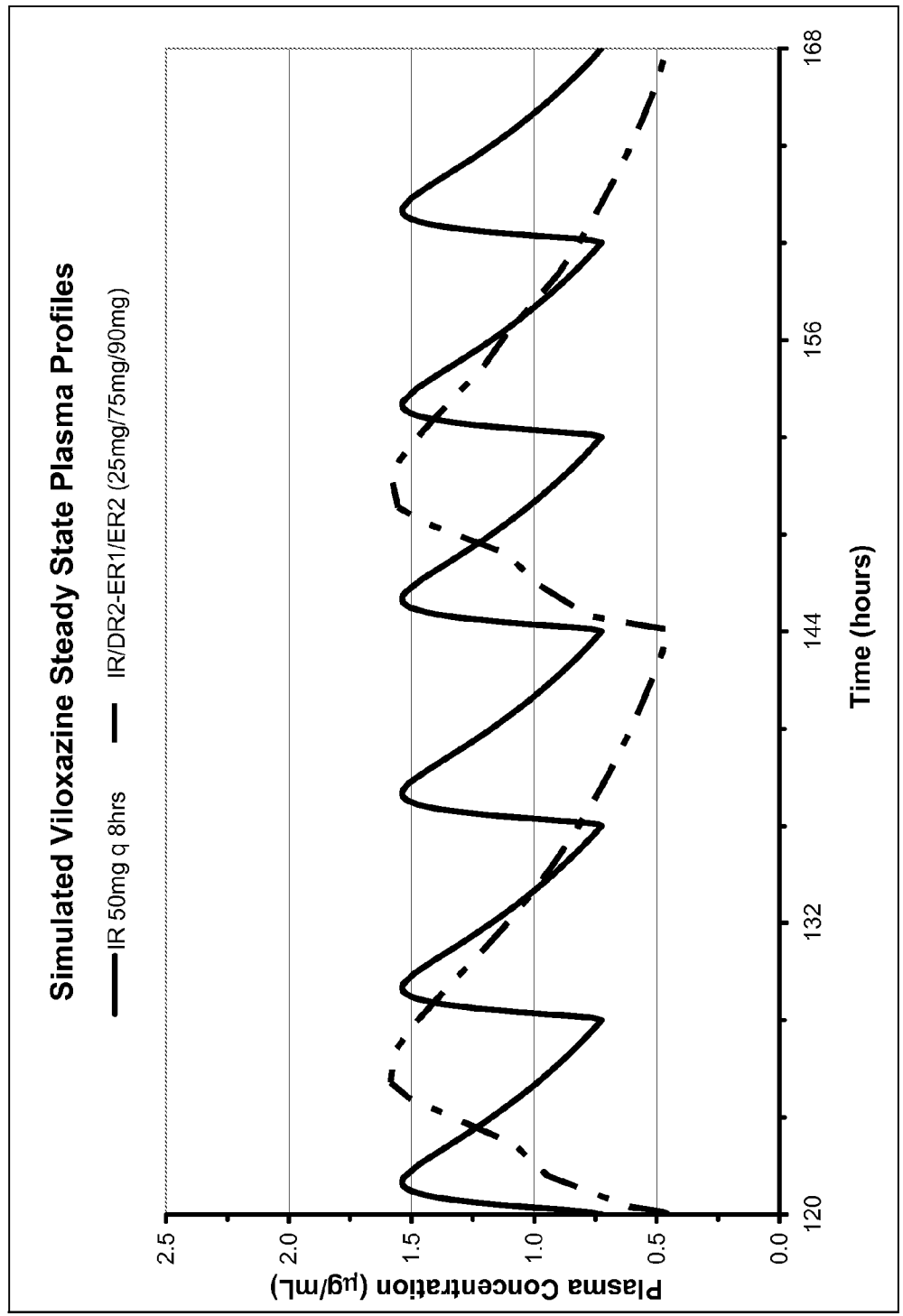
FIG. 22 shows simulated viloxazine steady state plasma profiles comparing an IR formulation dosed 50 mg every 8 hours daily, to the extended-release composition of Example 18.

FIG. 22 presents the comparison of the steady state simulated plasma profiles for an immediate-release 50 mg viloxazine dosage form dosed every 8 hours (TID) to that of an extended-release viloxazine formulation composition dosed qd. The ER composition contains 25 mg IR pellets, 75 mg of DR2-ER-1 pellets (a hypothetical composition of delayed-release of ER1 pellets) and 90 mg of ER-2 pellets. Pharmacokinetic analysis of the simulated profile for a dosing cycle of 24 hours ($AUC_{tau}$) estimated that the systemic in vivo exposure for this extended-release composition would be 88% of the systemic exposure achieved with this IR dosing scheme.

Example 19

In Silico Modeling for Gastric Retentive Extended-Release (GR-ER) Tablet Formulation In silico modeling was conducted using GastroPlus™ (copyright 2001-2010 Simulations Plus Inc.) to develop a simulated plasma concentration profile for a hypothetical gastric retentive extended-release (GR-ER) tablet formulation concept. All formulation doses used were as viloxazine base.

The GR-ER tablet (dose strength 150 mg) is designed to be retained in the stomach for up to 4 hours after ingestion after which the remaining dosage form and all undissolved drug is released into the duodenum to transit through the gastrointestinal tract. The in-vitro dissolution profile used for the GR-ER tablet releases 80% of the dose of drug contained in the dosage form in approximately 10 hours.

Figure 23:
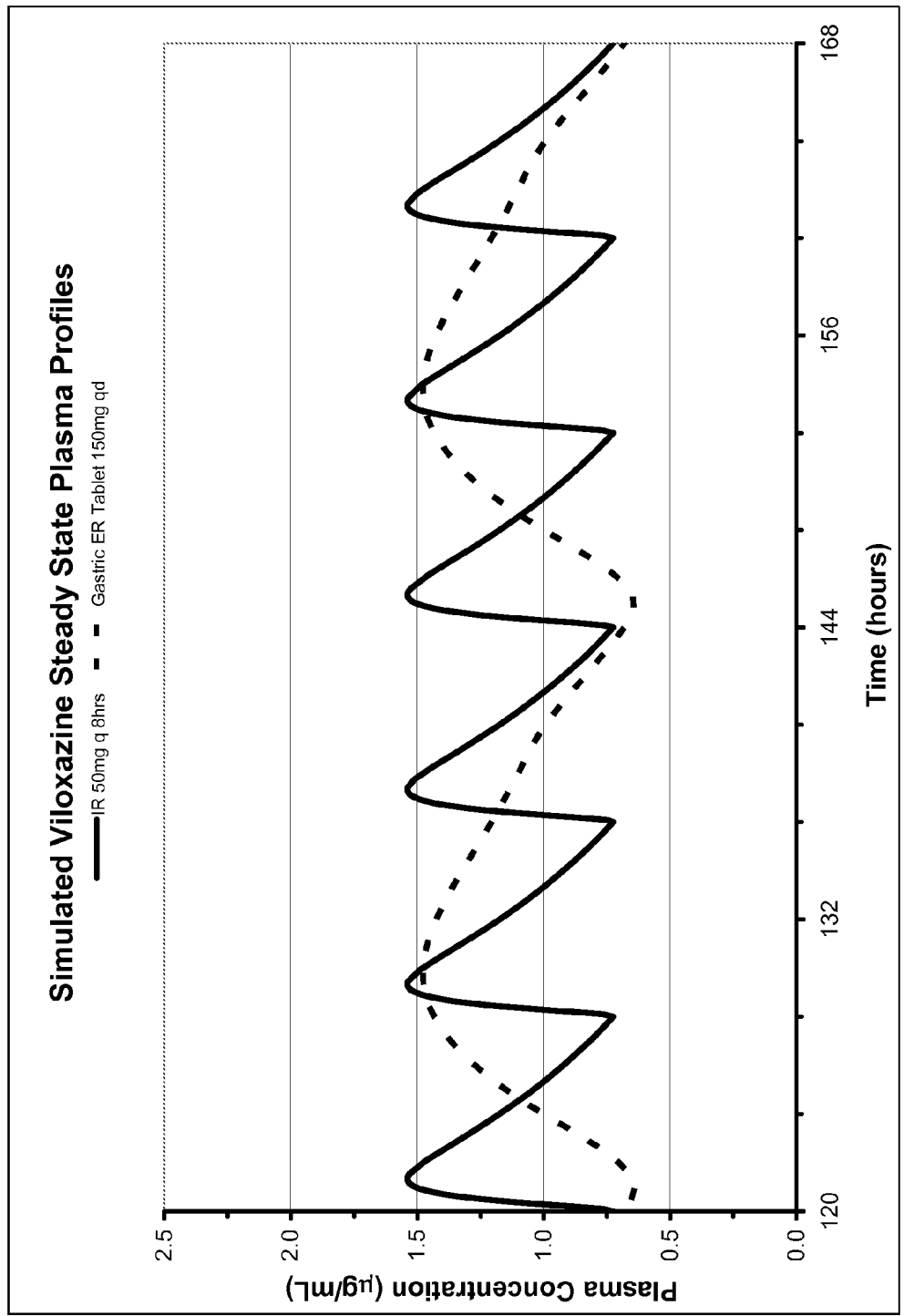
FIG. 23 shows simulated viloxazine steady state plasma profiles comparing an IR formulation dosed 50 mg every 8 hours daily to a 150 mg gastric retentive extended-release tablet dosed once daily (Example 19).

FIG. 23 presents the comparison of the steady state simulated plasma profiles for an immediate release 50 mg viloxazine dosage form dosed every 8 hours (TID) to that of the GR-ER tablet composition dosed qd. Pharmacokinetic analysis of the simulated profile for a dosing cycle of 24 hours ($AUC_{tau}$) estimated that the systemic in vivo exposure for this GR-ER tablet composition would be 98% of the systemic exposure achieved with this IR dosing scheme.

Example 20

Viloxazine Capsules Containing Extended Release Pellets

The Viloxazine ER-F Pellets of Example 14 (Table 13) can be filled into size 00 capsules to produce a 300 mg viloxazine dose strength capsule or into size 000 capsules to produce a 400 mg viloxazine dose strength capsule (viloxazine doses as viloxazine base).

Example 21

Additional Matrix Tablet Formulations

Final tablet blend PD0348-075 (Table 16) was compressed into 50 mg dose strength tablets (dose as viloxazine base). Tablets were evaluated for average viloxazine content (n=2) and drug release testing at pH 1.1 and pH 6.8. The average content value was 99.2% label claim. The drug release profiles at pH 1.1 and pH 6.8 exhibited $t_{80}$ values of approximately 8 hours.

TABLE 16

Formulation PD0348-075

| Compressed Tablet [a] | Usage (% w/w) |
|---|---|
| Viloxazine Hydrochloride | 28.84 |
| METHOCEL ™ K15M Premium CR | 29.99 |
| POLYOX ™ WSR 303 | 19.99 |
| Avicel ® PH 101 | 14.14 |
| Methocel E5 Premium LV | 3.00 |
| Talc, USP | 3.04 |
| Magnesium Stearate, NF | 1.00 |
| Total | 100 |

[a] Drug load 29% (w/w) viloxazine hydrochloride

The formulation in Table 16 can be modified as described in Table 17 to potentially extend the drug release profile $t_{80}$ value beyond 8 hours.

TABLE 17

Formulation PD0348-075

| Compressed Tablet [a] | Usage (% w/w) |
|---|---|
| Viloxazine Hydrochloride | 25.00 |
| METHOCEL ™ K100M Premium CR | 35.00 |
| POLYOX ™ WSR 303 | 30.00 |
| Avicel ® PH 101 | 5.00 |
| Methocel E5 Premium LV | 3.00 |
| Talc, USP | 1.00 |
| Magnesium Stearate, NF | 1.00 |
| Total | 100 |

[a] Drug load 25% (w/w) viloxazine hydrochloride

Example 24

High Drug Load Extended Release Pellet Formulation

A higher drug load extended release pellet formulation can be produced by coating the immediate release pellet formulation produced by the granulation described in Table 6 of Example 5 with Surelease® E-7-19010 to 5% (w/w). The resulting pellet dosage form will have a viloxazine hydrochloride drug load of 71% (w/w).

Example 25

Extended Release Pellet Formulation

Figure 24:
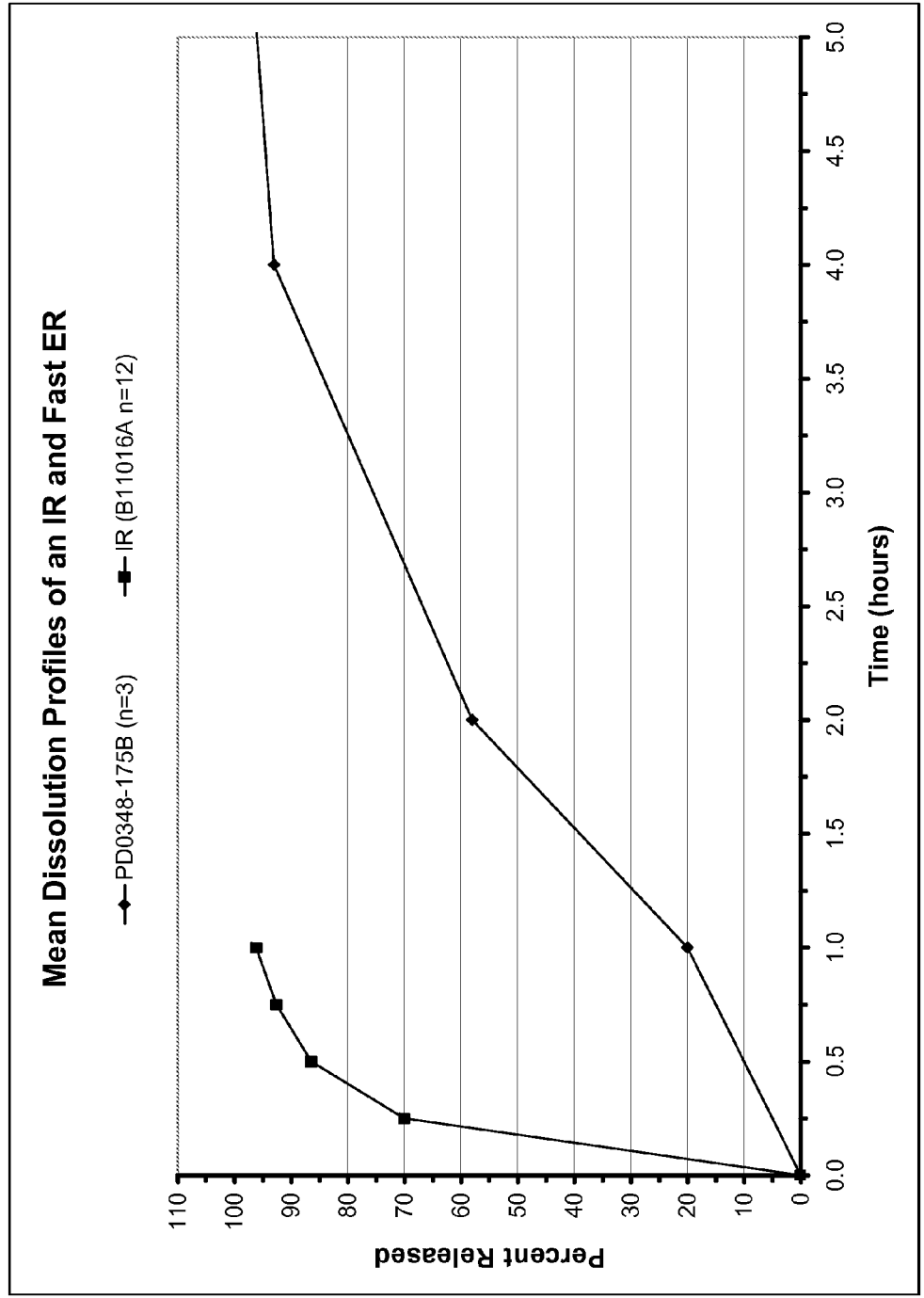
FIG. 24 shows the mean dissolution profile (n=12) at pH 6.8 for the immediate release capsule formulation of Example 15 compared to the mean dissolution profile (n=3) of the extended release pellet formulation PD0348-175B (Example 25).

The immediate release pellets seal coated with Opadry® II White (33G28523) to a 5% weight gain were subsequently coated with EUDRAGIT® NE 30 D containing Povidone, USP (at a ratio of 9:1 EUDRAGIT® NE 30 D solids to Povidone, USP solids) to a weight gain of 10% (w/w) producing an extended release pellet formulation exhibiting a $t_{80}$ value of between 3 hours and 4 hours (FIG. 24).

Example 26

Clinical Study to Evaluate the Efficacy of Viloxazine in Adults with ADHD

A randomized, double blind, multicenter, placebo controlled clinical study was conducted to evaluate the efficacy of viloxazine in adults with ADHD. During the five week treatment phase subjects were administered two 50 mg viloxazine capsules (formulation of Example 13, Table 9) TID for a total daily dose of 300 mg viloxazine base. Subjects not tolerating the 300 mg/day dose were allowed at any time of the treatment phase to down titrate to 1 capsule TID for a total daily dose of 150 mg viloxazine base. Subjects completing the study had the option to enroll in the PK portion of the study where at the last clinic visit plasma samples were obtained from each subject pre-dose and following the administration of either 50 mg viloxazine (4 subjects) or 100 mg viloxazine (14 subjects) representing the first dose of the next dosing day. Plasma samples were obtained up to six hours following dosing.

The results of the study indicated that the steady state viloxazine plasma levels achieved at both the 150 mg and the 300 mg total daily dose demonstrated clinical efficacy. The mean plasma concentration observed for the 4 subjects receiving the 50 mg viloxazine dose at the last clinic visit ranged from 0.5 μg/mL to 1.6 μg/mL over the 6 hour sampling period. The mean plasma concentration observed for the 14 subjects receiving the 100 mg viloxazine dose at the last clinic visit ranged from 0.5 μg/mL to 2.1 μg/mL over the 6 hour sampling period.

Example 27

Viloxazine Granulation Formulation for Preparing Extruded/Spheronized Pellets

Granulation formulation (Table 18) was manufactured employing a process similar to that used for formulation PD348-099 of Example 5. The granulation was subsequently processed into pellet lot PD0385-010 by extrusion and spheronization. A seal coat of Opadry® II White (33G28523) was applied to the pellets using a Wurster process on a GPCG-1. The seal coated pellet lot PD0385-030 was processed into extended release pellets (lot PD0385-033) by the application of an XR coating system of Surelease® E-7-19010 containing the pore former, METHOCEL™ E5 Premium LV at the ratio of 9:1 using a Wurster process on a GPCG-1.

TABLE 18

Granulation Formulation PD0385-010

| Component | Usage (% w/w) |
|---|---|
| Viloxazine Hydrochloride | 71.30 |
| Avicel ® PH 101 | 14.30 |
| Dicalcium Phosphate Dihydrate, USP | 9.60 |
| METHOCEL ™ E5 Premium LV | 1.40 |
| Povidone, USP (K-value 30) | 1.00 |
| Talc, USP | 2.40 |
| Total | 100 |

Example 28

Multiparticulates of Viloxazine by Drug Layering—Lower Potency Pellet

Multiparticulate pellets of viloxazine were prepared using a drug layering technique. The drug layering dispersion formulation (Table 19) was prepared by first dissolving 2.18 g of METHOCEL™ E5 Premium LV in 1436.92 g of water with the aid of a propeller mixer. The viloxazine hydrochloride (311.53 g) was then added to the METHOCEL™ E5 Premium LV solution and mixed for approximately one hour.

TABLE 19

Drug Dispersion Formulation PD0387-085

| Component | Usage (% w/w) |
|---|---|
| Viloxazine Hydrochloride | 17.43 |
| METHOCEL ™ E5 Premium LV | 2.18 |
| Water | 80.39 |
| Total | 100 |

Figure 25:
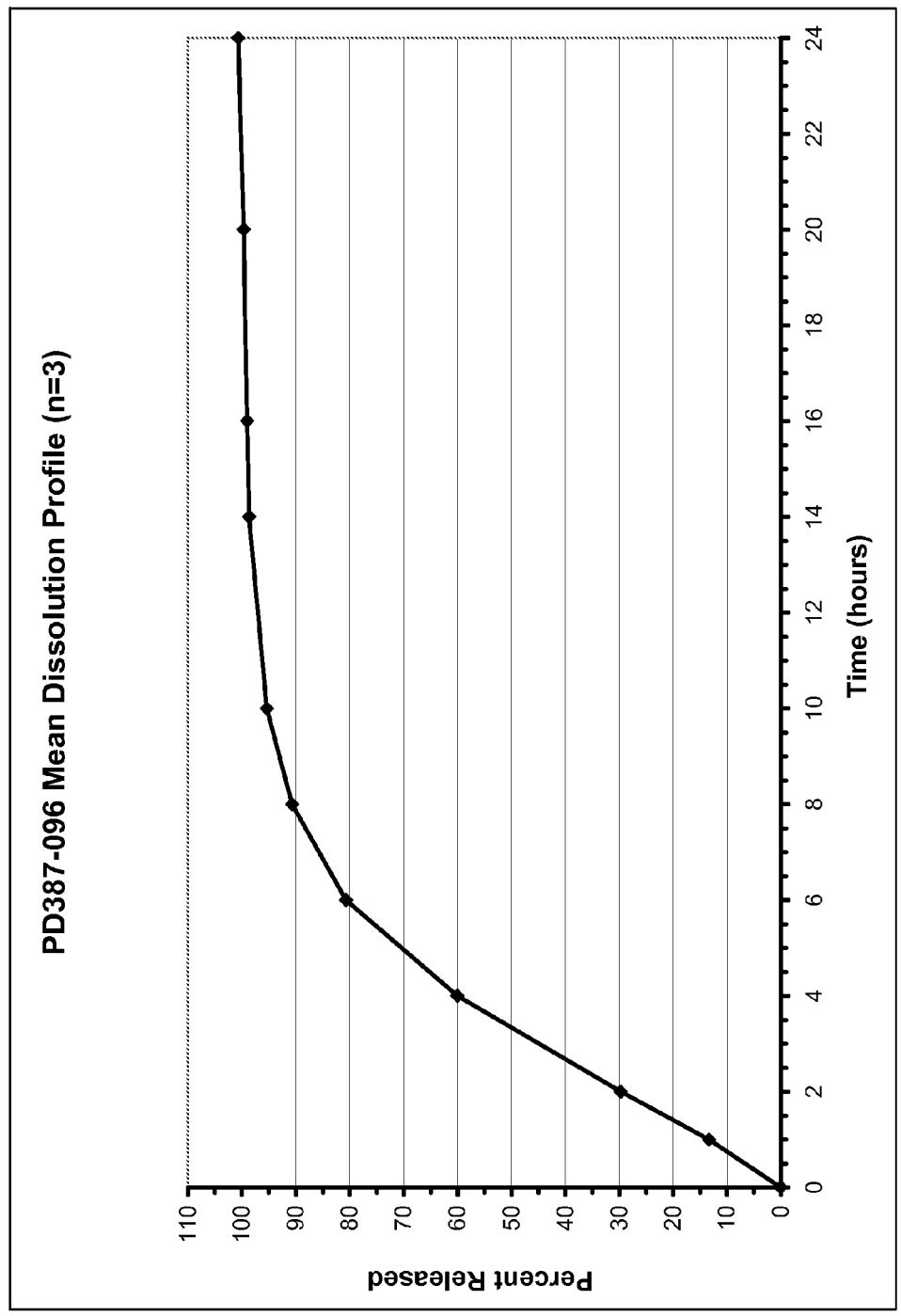
FIG. 25 shows the mean dissolution profile (n=3) of 150 mg dose strength pellets (PD0387-096) at pH 6.8 (Example 28).

After mixing, the dispersion was screened through an 80 mesh sieve and then using a Wurster process on a GPCG-1 the dispersion was applied to 1000 g of sugar spheres (30/35 mesh) producing the drug layered pellet lot PD0387-085. The finished drug layered pellet lot had a drug content value of 20% (w/w). The drug layered pellet lot was then seal coated using a Wurster process on a GPCG-1 to a 5% (w/w) coating level with Opadry® II White (33G28523) resulting in a drug content value of 18.7% (w/w). The seal coated pellet lot (PD0387-094) was processed into the extended release pellet lot PD0387-096 by the application of the XR coating system of Surelease® E-7-19010 containing the pore former, METHOCEL™ E5 Premium LV at the ratio of 9:1 to a level of 14% (w/w) using a Wurster process on a GPCG-1. The extended release pellets were oven cured at 70° C. for 48 hours. The drug content value for the extended release pellet lot was determined to be 16% (w/w). The extended release pellet lot was also evaluated for drug release (FIG. 25). The drug release profile was near zero-order release over the interval of 0 hours to 6 hours with a $t_{80}$ value of 6 hours.

Example 29

Multiparticulates of Viloxazine by Drug Layering—Higher Potency Pellet

Figure 26:
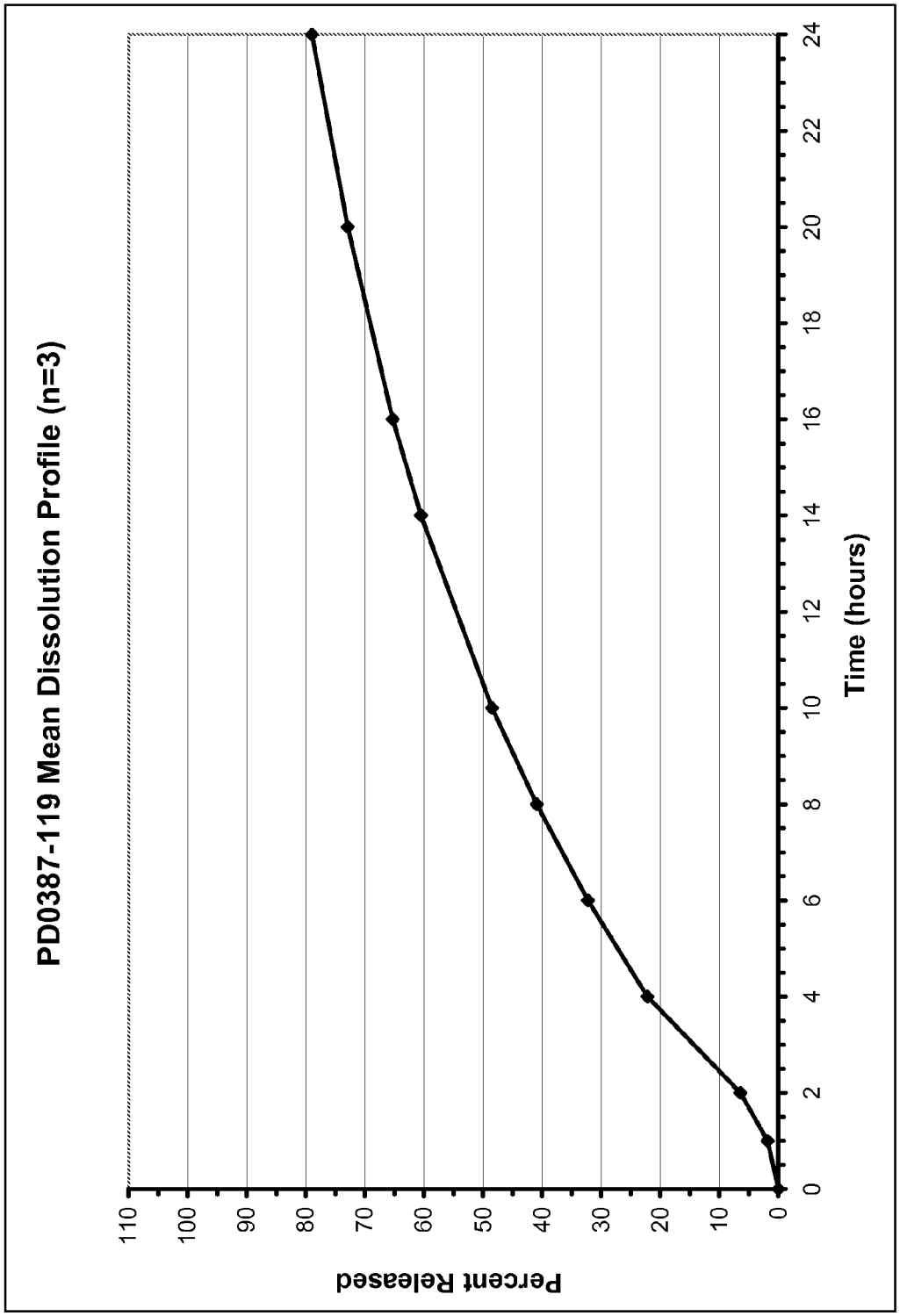
FIG. 26 shows the mean dissolution profile (n=3) of 150 mg dose strength pellets (PD0387-119) at pH 6.8 (Example 29).

The drug layered pellet lot PD0387-113 was produced by drug layering the drug dispersion formulation listed in Table 19 on 30/35 mesh sugar spheres using a Wurster process on a GPCG-1 to the drug content value of 41% (w/w). The drug layered pellet lot was then seal coated using a Wurster process on a GPCG-1 to a 5% (w/w) coating level with Opadry® II White (33G28523) resulting in a drug content value of 39% (w/w). The seal coated pellet lot (PD0387-117) was processed into the extended release pellet lot PD0387-119 by the application of the XR coating system of Surelease® E-7-19010 containing the pore former, METHOCEL™ E5 Premium LV at the ratio of 9:1 to a level of 16% (w/w) using a Wurster process on a GPCG-1. The extended release pellets were oven cured at 60° C. for 48 hours and the drug content value and the drug release profile were determined. The drug content value was determined to be 33% (w/w). The drug release profile (FIG. 26) exhibited a $t_{80}$ value of 24 hours Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

The invention claimed is:

1. A pharmaceutical formulation, comprising:
    (a) an immediate release (IR) component comprising an inert core and a layer comprising viloxazine and, optionally, a pharmaceutically acceptable excipient, surrounding the core, and
    (b) an extended release (XR) component comprising: (i) an inert core, (ii) a first layer comprising viloxazine and, optionally, a pharmaceutically acceptable excipient, surrounding the core, and (iii) a second layer comprising a release rate controlling compound and a pore former in a weight ratio of 19:1 to 8.5:1.5, respectively, surrounding the first layer,
    wherein the pore former is selected from the group consisting of povidone, hypromellose, hydroxyethyl cellulose, hydroxypropyl cellulose, and organic acids,
    wherein the release rate controlling compound is selected from the group consisting of ethylcellulose; cellulose acetate; cellulose acetate butyrate; waxes; hydrogenated vegetable oils; glyceryl behenate; glyceryl palmitostearate; PEG glyceryl esters; poly(ethyl acrylate-co-methyl methacrylate) ethyl acrylate methyl methacrylate copolymer; poly(ethyl acrylate-co-methyl methacrylate-cotrimethylammonioethyl methacrylate chloride); polyvinyl acetate; cellulose acetate propionate, and combinations thereof, and is present in an amount of from 5% (w/w) to 65% (w/w) of the XR component,
    wherein the formulation comprises, as a percentage of the total formulation, 25% (w/w) to 75% (w/w) viloxazine,
    wherein the viloxazine is released immediately and continuously upon administration, and
    wherein at least 80% of the viloxazine or salt thereof in the formulation is released from the formulation over a period of time of at least 2 hours in vitro.

2. The formulation of claim 1, further comprising a hydrophilic compound that is selected from the group consisting of hydroxypropyl cellulose; hydroxypropyl methyl cellulose; methyl cellulose; polyethylene oxide; acacia; acrylic acid derivatives; alginic acid, its salts and derivatives thereof; hydroxyethyl cellulose; povidone; carrageenan; carboxymethylcellulose; tragacanth; polyvinyl alcohol; xanthan gum, and combinations thereof.

3. The formulation of claim 1, wherein the release rate controlling compound is selected from the group consisting of ethylcellulose; cellulose acetate; cellulose acetate butyrate; polyvinyl acetate; cellulose acetate propionate, and combinations thereof.

4. The formulation of claim 1 wherein the release rate controlling compound is present in an amount of 5% (w/w) to 18% (w/w) of the extended release component.

5. The formulation of claim 1, wherein the extended release component is in the form of a plurality of particles.

6. The formulation of claim 1 for once-a-day administration.

7. The formulation of claim 1 for twice-a-day administration.

8. The formulation of claim 1, comprising from 10 mg to 800 mg of viloxazine.

9. The formulation of claim 1, wherein the viloxazine comprises viloxazine hydrochloride.

10. The formulation of claim 1, wherein the formulation provides for a maximum steady state plasma concentration ($C_{max}$) of viloxazine which is higher than the minimal therapeutically effective concentration and is in the range of 50% to 125% relative to the maximum plasma concentration produced by administration of viloxazine as an IR formulation TID or BID.

11. The formulation of claim 1, wherein the formulation provides for relative steady state area under the viloxazine plasma concentration time profiles for a 24 hour dosing interval ($AUC_{tau}$) in the range of 80% to 125% as compared to viloxazine administered as an immediate release formulation TID or BID.

12. The formulation of claim 1 in a dosage form selected from tablets, capsules, beads, granules, powders, caplets, troches, sachets, cachets, pouches, and sprinkles.

13. The formulation of claim 1 comprising at least two extended release components, wherein each extended release component has its own rate of release.

* * * * *